United States Patent
Riley

(10) Patent No.: US 7,017,294 B2
(45) Date of Patent: Mar. 28, 2006

(54) WRISTBAND/CINCH WITH INBOARD LABEL ASSEMBLY BUSINESS FORM AND METHOD

(75) Inventor: James R. Riley, St. Louis, MO (US)

(73) Assignee: Laser Band, LLC, St. Louis, MO (US)

( * ) Notice: Subject to any disclaimer, the term of this patent is extended or adjusted under 35 U.S.C. 154(b) by 0 days.

(21) Appl. No.: 10/627,135

(22) Filed: Jul. 25, 2003

(65) Prior Publication Data

US 2004/0068906 A1 Apr. 15, 2004

Related U.S. Application Data

(63) Continuation-in-part of application No. 10/283,777, filed on Oct. 30, 2002, which is a continuation-in-part of application No. 10/256,758, filed on Sep. 27, 2002.

(51) Int. Cl.
*A44C 5/00* (2006.01)

(52) U.S. Cl. .......................... 40/633; 283/75
(58) Field of Classification Search ..................... None
See application file for complete search history.

(56) References Cited

U.S. PATENT DOCUMENTS

| | | | | |
|---|---|---|---|---|
| 922,948 A | * | 5/1909 | Portmare | 283/80 |
| 3,197,899 A | | 8/1965 | Twentier | |

(Continued)

FOREIGN PATENT DOCUMENTS

| | | |
|---|---|---|
| GB | 960859 | 6/1964 |
| GB | 2045718 | 11/1980 |
| GB | 2 160 492 A | 12/1985 |
| JP | 2003066849 | 3/2003 |
| JP | 2003157010 | 5/2003 |

| | | |
|---|---|---|
| WO | WO 96/12618 | 5/1996 |

OTHER PUBLICATIONS

Disaster Management Systems, Inc., Triage Tag, Copyright 1996, Pomona, California.

(Continued)

*Primary Examiner*—Joanne Silbermann
(74) *Attorney, Agent, or Firm*—Thompson Coburn, LLP

(57) ABSTRACT

A business form particularly adapted for generalized use, although it may be used in a medical or hospital environment includes in a first embodiment a wristband that is provided with a laminate backing including a tab portion at the opposite end of a free end, with the tab portion having a cinch slot through which the free end is inserted for securing the wristband about a person's appendage. Several self adhering labels are provided inboard of the tab and may be individually separated from the wristband. The labels and the wristband may each be imprinted with identifying indicia such as bar coding. A second embodiment of the invention includes a page sized form with one or more self laminating wristbands readily separable from a carrier with each wristband comprised of a layer of face stock and a laminate, with the wristband including a printable face stock region die cut into the face stock and a strap portion, a laminating portion, and a cinch die cut into the laminate layer. The laminating portion includes two halves which fold together about a fold line to enclose the face stock, with the strap portion extending from one of said halves. The cinch comprises two slots which may both be located outboard of the face stock, or on both sides of the face stock. The free end of the strap may be adhered in place by folding over one of the slots, or by adhering a patch of adhesive carried at the tip of the free end. The face stock may be extended to the edge of the cinch slot to shield the strap from contacting adhesive. Any of the wristband constructions may be provided on a page sized sheet along with a plurality of self adhering labels, in any of a number of configurations, to suit any particular application, as desired by a user.

11 Claims, 17 Drawing Sheets

U.S. PATENT DOCUMENTS

| | | |
|---|---|---|
| 4,612,718 A | 9/1986 | Golub et al. |
| 4,627,994 A | 12/1986 | Welsch |
| 4,682,431 A | 7/1987 | Kowalchuk |
| 4,696,843 A | 9/1987 | Schmidt |
| 4,854,610 A | 8/1989 | Kwiatek |
| 4,914,843 A | 4/1990 | DeWoskin |
| 4,956,931 A | 9/1990 | Selke |
| RE33,616 E | 6/1991 | Welsch |
| 5,026,084 A | 6/1991 | Pasfield |
| 5,045,426 A | 9/1991 | Maierson et al. |
| 5,135,789 A | 8/1992 | Schmidt |
| 5,227,004 A | 7/1993 | Belger |
| 5,318,326 A | 6/1994 | Garrison |
| 5,370,420 A | 12/1994 | Khatib et al. |
| 5,383,686 A | 1/1995 | Laurash |
| 5,418,026 A | 5/1995 | Dronzek, Jr. et al. |
| 5,427,416 A | 6/1995 | Birch |
| 5,486,021 A | 1/1996 | Laurash |
| 5,486,436 A | 1/1996 | Lakes |
| 5,509,693 A | 4/1996 | Kohls |
| 5,509,694 A | 4/1996 | Laurash et al. |
| 5,518,787 A | 5/1996 | Konkol |
| 5,524,934 A | 6/1996 | Schwan et al. |
| 5,547,227 A | 8/1996 | Laurash et al. |
| 5,586,788 A | 12/1996 | Laurash |
| 5,595,404 A | 1/1997 | Skees |
| 5,598,970 A | 2/1997 | Mudry et al. |
| 5,601,313 A | 2/1997 | Konkol et al. |
| 5,630,627 A | 5/1997 | Stewart |
| 5,637,369 A | 6/1997 | Stewart |
| 5,648,143 A | 7/1997 | Mehta et al. |
| 5,653,472 A | 8/1997 | Huddleston et al. |
| 5,662,976 A | 9/1997 | Popat et al. |
| 5,687,903 A | 11/1997 | Akridge et al. |
| 5,933,993 A | 8/1999 | Riley |
| 6,000,160 A | 12/1999 | Riley |
| 6,006,460 A * | 12/1999 | Blackmer .................... 40/300 |
| 6,016,618 A | 1/2000 | Attia et al. |
| 6,053,535 A | 4/2000 | Washburn et al. |
| 6,067,739 A | 5/2000 | Riley |
| 6,071,585 A | 6/2000 | Roth |
| 6,159,570 A | 12/2000 | Ulrich et al. |
| 6,303,539 B1 | 10/2001 | Kosarew |
| 6,331,018 B1 | 12/2001 | Roth et al. |
| 6,361,078 B1 | 3/2002 | Chess |
| 6,409,871 B1 | 6/2002 | Washburn et al. |
| 6,438,881 B1 | 8/2002 | Riley |
| 6,510,634 B1 | 1/2003 | Riley |
| 6,517,921 B1 | 2/2003 | Ulrich et al. |

OTHER PUBLICATIONS

Maryland Department of Transportation, Maryland Emergency Medical Services, Triage Tag, Copyright MIEMMS 1999, Maryland.

Patent Cooperation Treaty; Partial International Search Report; Sep. 13, 2004.

Avery Dennison DuraCard™.

Avery® Laminated Identification Cards #5361.

Brochure entitled: "Color-Bar®—Click Strip™ Labeling System"; Smead Manufacturing Company; date unknown; Form No. SSS-CS-00.

Brochure entitled: "Color-Bar® Folders"; Smead Manufacturing Company; date unknown.

Brochure entitled: "Integrated Document Management Software"; Smead Manufacturing Company; date unknown; Form No. SLI-95.

Catalog entitled: "Reseller Catalog No. One"; Smead Software Solutions™; date unknown; Form No. SSS-RC1-00.

Sample of Standard Register Labels.

Standard Register, *P.S. Magazine*, Fall 1998, Dayton, Ohio.

Gretchen Berry, "Wrist Watch," *Advance for Healthcare Information Professionals*, Feb. 15, 1999.

Sample of Standard Register Label.

"Yes, Sir, That's My Baby!," *Material Management in Health Care*, Feb. 1999, vol. 8, No. 2, Health Forum, Inc.

Patent Cooperation Treaty; Partial International Search Report; May 24, 2005.

* cited by examiner

WRISTBAND/CINCH WITH INBOARD LABEL ASSEMBLY BUSINESS FORM AND METHOD

CROSS REFERENCE TO RELATED APPLICATION

This application is a continuation-in-part to Ser. No. 10/283,777, filed Oct. 30, 2002, currently pending, which is a continuation-in-part of Ser. No. 10/256,758, filed Sep. 27, 2002, currently pending, the disclosures of which are incorporated herein by reference.

BACKGROUND AND SUMMARY OF THE INVENTION

There are many situations where it would be convenient to have available a way to separately identify a person, such as a health care patient, with his/her possessions or other related items with which the person needs to be associated. As this is written, the recent events of the tragedy of Sep. 11, 2001 have provided a glaring example of one such situation. In that situation, it became evident that there was no convenient way to associate people desperately in need of health care with their belongings. Even more horrifying was the need to identify body parts, tag them, and assemble some kind of data base that could be used to sort through the confusion and chaos created on that terrible day. Under those circumstances, and many other similar emergency circumstances, the health care workers and the emergency workers are under tremendous time pressure, with protective clothing such as gloves being used to avoid personal danger to themselves, to sort through what is presented to them in the way of victims needing medical attention, their possessions including valuables, and a need to communicate with their family. The environment is usually hostile, with what may be fire, flying debris, collapsing buildings, un-breathable air, etc. which makes it quite different from a usual hospital or other controlled environment and makes handling any "standard" form imminently more difficult.

Another aspect to the situation that must be considered is that it is not uncommon for different care takers to handle a single victim. Generally, when a victim is first attended, he is categorized for the nature and extent of his injuries. Then, in those situations where there is a mis-match between the number of victims and the number of medical personnel, the most severely injured are attended to first and the remainder are treated as time becomes available. This is routine, and an attempt to minimize loss of life in what can be a desperate situation. Thus, it is commonly required to "triage" the victims, and then identify them in some way that makes it immediately apparent to medical workers just what their medical situation is. This sounds easy, but in the chaos of these situations, even with medical personnel who are well trained, there can be lost time in this process and if a good strategy is not used for this classifying, victims can be mis-identified or their status not readily ascertainable after classification, so that the precious time of these "angels of mercy" can be needlessly wasted as they move from one victim to another.

This type of emergency situation creates needs that are unique, beyond the needs of a form intended for use in a clean environment available in an emergency room. As mentioned, medical personnel are usually wearing gloves and in a hurry. Thus, any form that would be used must be adapted to be easily handled with clumsy fingers. There is no time for instruction, so the form must be virtually intuitive for use. There are commonly fluids present, unfortunately most often blood and other body fluids, so the form must be protected. There needs to be a simple, fast, fool-proof way to apply the form to the victim, and his possessions, with a reliable way to link them together. There is a further need to be able to quickly collect the identifying information from the form as it is attached to a victim so he may be processed quickly and the information accurately collected. The identifying information commonly needs to be thought out in advance, and might even be pre-coded to mesh with the triage operation so that merely knowing the identifying information conveys some information about victim medical status. And, there is desirably some flexibility available in use of the form to accommodate different victim conditions.

Still another need exemplified by this tragedy is that of providing information to families and other loved ones. After the September 11 event, it was well publicized that family members and others resorted to walking the streets, following any rumor, visiting geographically separated emergency medical care sites, asking for information if not finding their loved one. This itself caused much anxiety and pain amongst the survivors. While not as critical as getting information about survivors to their families, this inability to assemble information created other problems including the inability to gauge the magnitude of the tragedy. A complete list of the survivors was impossible to assemble for days, even though information was individually available by then. There just was not a convenient way to assemble this information in a common data base. Some attempts were made to use the internet, but inaccuracies abounded and the information posted there was soon being ignored, at least part due to the lack of confidence in that information.

To solve these and other needs in the prior art, the inventor herein has previously developed a business form as disclosed and claimed in the parent in several embodiments and a method incorporating the use of that form that have particular application to these kind of medical emergency situations. Briefly, a first embodiment of the form comprises a carrier sheet of paper stock, with a wristband/label assembly die cut thereinto for separation from the carrier sheet. The paper stock is preferably pre-printed with identifying indicia, color coded and covered top and bottom with a layer of protective coating which may preferably be a poly plastic. The wristband/label assembly may be dry adhered to a bottom layer of a carrier film so that it may be readily separated from the carrier without retaining any adhesive. The wristband portion of the assembly may have a tab on one end and a long strap portion which, to be assembled, is wrapped around an object such as a victim's wrist, looped back through a "cinch" comprising a slot in the tab and then adhered to itself by an adhesive portion at the end of the strap portion. The tab preferably has a plurality of individually separable labels die cut thereinto, with each of the labels and the wristband having an identifying indicia which may preferably be a bar code. In the embodiment disclosed in one of the parent applications, the slot is inboard of the labels while in the embodiment first disclosed herein the slot is outboard of the label carrying portion of the tab. Furthermore, the embodiment first disclosed herein is narrower, more streamlined, and eliminates the medical indicia making the wristband/label form more universally applicable as a simple identifier.

In use, the wristband/label assembly of the parent is separated from the carrier, carrying the tab filled with labels, and the strap portion. The cinch slot is die cut and formed as the assembly is separated with its filler piece adhered to remain behind with the bottom film carrier sheet. The strap portion has its end covered with a laminated bottom patch so that as it separates it carries with it a peel away covering over its end having the adhesive. After being separated from the carrier, the wristband/label assembly has a protective layer over both its top and bottom for resisting fluid contamination and the tab has a label section which may be perforated for separation from the wristband. Each of the labels are individually separable and carry the identifying indicia. The wristband may preferably be color coded, and the forms may be made in sets with multiple ones of each of a number of different colors. Alternately, color coded, perforated tabs may be provided at the end of the tab portion, such that the medical technician need only separate one or more tabs, leaving as the outside tab the correct one to visually indicate the condition of the victim. A blank tab is preferably provided at the very edge of the tab portion so that no one would mistakenly interpret the failure to separate a tab as a conscious attempt at indicating medical condition. In still another embodiment, the medical indicia may be eliminated and the strap portion streamlined to allow for a more generic use of the form for merely indicating identity of the patient or other individual for other purposes than medical. The wristband may be readily applied by wrapping the strap portion about the person's appendage, slipping it through the "cinch" comprising the slot to tighten it about the appendage, pulling it tight, and then folding the strap portion back onto itself for attachment with the adhesive after removing the peel away covering.

In a second embodiment as shown and described in the parent, the wristband/label assembly is pre-printed and formed in its final configuration, with a tab/label portion and a strap portion made from preferably four layers. A top, clear film layer overlies and protects a face stock layer upon which the pre-printed information including bar codes and color "condition" codes are applied. A layer of adhesive then joins the face stock to a base film material, again to protect the face stock in use. In either embodiment, more than one slot, or "cinch" point, may be provided to allow for a snug fit to different sized body parts. Also, more or fewer bar coded labels, of smaller or larger size, may be selected for use to suit a designer's preferences or user's needs. And, as explained above, the slot may be outboard of the label portion, thereby making the wristband easier to attach to a person, and without sacrificing integrity as the underlying web provides more than adequate strength for maintaining the wristband in its intended use.

In the method of the parent invention, once a form has been applied to a victim, and the victim thus associated with an identifying indicia, and his possessions properly tagged, software pre-loaded into a computer may then receive as much information about the victim as is available. Items of information might include his associated color code (which would preferably be indicative of his medical condition), his name and other demographic information, his statistics such as height, weight, race, etc., more detailed information as to the nature of his injuries or condition, the location where this victim is processed, and other appropriate information. The computer may then go on-line, or be on-line, and the data set up-linked to a web site. A plurality of treatment centers could each be simultaneously processing victims, and transmitting data to the web site for ready access and display to anyone interested in learning about a victim's condition. As a victim's condition changes, updated information could be provided to the web site, although it is considered by the inventor that the method of the parent is most effective in providing early information as fast as possible to the most people. Updated information could be available more directly as a victim's family locates and goes to where treatment is being given. Security in the web site and data links would prevent any mischief from occurring which might compromise the integrity of the data such that families could rely on the information posted.

As can be appreciated by those of ordinary skill in the art, there is unfortunately need for the parent invention given the heightened risk of terrorism that the world now faces, and along with that arises an increased need to facilitate not only the quick processing of victims but also the task of collecting and disseminating information about these victims. The parent invention addresses these needs, which in actuality are long felt needs exacerbated by our changing times. Accordingly, the foregoing provides a brief description of some of the advantages and features of the parent invention. A fuller understanding may be attained by referring to the drawings and description of the preferred embodiment of the parent which follow for the readers understanding.

The inventor has taken several of the features of the parent invention and used it to build onto his prior work in the wristband art as exemplified by the following patents issued to the inventor herein, the disclosures of which are incorporated herein by reference: U.S. Pat. Nos. 6,438,881; 6,067,739; 6,000,160; and others still pending. In his invention as disclosed and claimed in the more recently filed second patent application referenced above, he has incorporated the "cinch" of the parent into a self laminating wristband form in a unique and non-obvious way to provide many advantages and features not hereto available. Although the second parent's invention is exemplified in several embodiments as explained in greater detail below, each of which has its own unique advantages and features, it represents a departure from the construction found in the inventors prior patents. Some of the differences include the use of a single, preferably narrow, strap portion extending generally from one side of the face stock region, with the cinch comprising a slot located on either side of the face stock and either adjacent the top or bottom portion of the laminating portion that overlies the face stock. With this construction, it is thought that several advantages are obtained over the wristband construction of his prior inventions. First, in this invention the inventor uses less face stock resulting in a smaller area of the form needing to be over-laminated. In other words, in the inventor's prior patented wristbands, virtually the entire length of the wristband comprised face stock, all of which was over-laminated. In the more recent parent invention, preferably only a "patch" of face stock is used which does reduce the amount of space for printing but which at the same time reduces the size of the over-lamination "patch" needed. This smaller over-lamination "patch" is much easier for a nurse or other medical professional to fold over and complete the assembly, and thus apply the wristband to the patient. A related advantage is that by eliminating the face stock from the "strap portion" that surrounds the patient's wrist, this strap portion may be narrower and formed from a single layer of the lamination (with no adhesive applied). This is more comfortable to the patient for several reasons. The strap is narrower, thereby being less likely to bind or press into the patient's skin as he moves his wrist in doing daily living activities. The strap is also thinner as it is formed from only a single layer and may thus be more flexible. In this construction, a thinner laminate may be used than in prior designs which increases the patient's comfort. Patient comfort is an important consideration as patient's in hospitals are generally uncomfortable to begin with, being out of their ordinary environment, and those in need of hospital care are generally infirm, older or younger such as prenatal, and their skin may be more sensitive than normal. So, this is an important design criteria.

Still another advantage comes through incorporation of the cinch in this design. The cinch preferably comprises a slot which may be located in one of several places in the wristband, but it offers several unique advantages. First, if need be, the cinch may be used to more easily apply the wristband to a patient as it gives the nurse a ready attachment fixture with which he/she is quite familiar, it being much like an ordinary belt worn by almost everyone, male and female. For those patients who may be uncooperative or thrashing about or otherwise resistive, applying the wristband amounts to getting the strap through the slot and after that is achieved the rest needed to be done is relatively simple. For those patients who need to be tightly banded, the cinch provides a ready means to tighten down the strap and keep it tight while the cinch and strap are adhered in place. This allows for a simpler built in adjustment in strap length than with the prior designs. The cinch may be located in one of several places in the band, and each location offers its own unique advantages. If located intermediate the face stock and the strap, the face stock is converted into a "hang tag" which hangs freely from the patient's wrist after it is applied. This aids the nurse in finding and reading the information printed on the face stock, and also makes it easier for her to read imprinted indicia on the face stock with a hand held bar code reader, for example, as the surface is flat. Also, with this arrangement, a smaller strap is readily provided for smaller wrists such as with new-born babies. If the slot is located outboard from the face stock, the face stock hugs the patient's wrist much more like a conventional wristband, and an extra area of fold over laminate may be used to adhere the strap in place, making for a more secure attachment. Either arrangement would be desirable depending on the particular application, and is left to the user's choice.

As alluded to above, the strap portion is adhered in one of several ways, depending on the embodiment chosen. If the cinch is intermediate the face stock and strap, the end of the strap has a patch of adhesive which is used to adhere it back onto itself after being threaded through the slot. With the cinch outboard of the face stock, an "extension" of laminate is used which may carry adhesive along with a fold line through the slot so that after the strap is threaded through the slot the extension may be folded about the fold line and "clamp" the strap in place with adhesive. This provides a second means for adhering the strap in place.

The face stock layer has a printable region or ply defined therein with a die cut while the lamination layer has three elements die cut in to it. The lamination layer has a strap portion, a laminating portion, and a cinch portion all die cut therein, with adhesive being applied to preferably the extreme end of the strap portion for securing the strap to itself after the wristband has been applied, adhesive applied to the lamination portion to substantially, and preferably entirely, surround and enclose the face stock printable region, and adhesive applied to a cinch portion (if located outboard of the face stock) for adhering to the strap portion after it is passed through the cinch. Adhesive may preferably be omitted from the portion of lamination that overlies the face stock to improve it's readability, both visually and for bar coding. In variations to this embodiment, the cinch, which is preferably a slot aligned generally perpendicular to the face stock, may be located in one of several places, either outboard of the face stock region or intermediate the face stock and the strap portion. When positioned outboard of the face stock, the cinch may also be located in one of two places either in an extension of the lamination adjacent a top portion or the bottom portion of the lamination portion. When positioned intermediate the face stock and strap portion, the cinch may be formed from a pair of slots located in both the top and bottom portion of the lamination portion. In this arrangement, adhesive is applied to join the top and bottom lamination portions, but it does not aid in holding the strap in position unless the nurse takes the time and is able to obtain the cooperation of the patient to thread the strap through only one of the slots before folding the lamination halves together to enclose the face stock. However, this is thought to be a less desirable attachment arrangement than first enclosing the face stock and then threading the strap through the slot.

As an added feature, the inventor has previously developed an extender which is also formed in the same two plies of material, with the extender comprising a length of laminate having a fold over or "clamshell" portion with adhesive at one end, and a patch of adhesive at its opposite end. The extender is sized preferably to be of the same width as the strap portion and is applied to the strap portion by use of the clamshell which clamps onto the strap portion and along its length, with the extender patch of adhesive serving the function of joining the strap. With the extender, the wristband may be used with larger patient's, conveniently, without being limited to the overall length of the form or carrier in which the wristband is formed.

In variations of these embodiments, the novel wristband of the more recent parent invention may be formed in a sheet with a plurality of self adhering, peel off labels, all of which may be printed with identifying indicia or information relating to the patient. Several wristbands of different size, or the same size, may also be formed on a single sheet, with or without labels. The extender may also be provided in any one or more of the variations, which are only limited by the perceived needs of users, and design choice.

As a further enhancement to his work with the two general categories of wristband/label forms with cinch, the inventor has modified the forms to provide even greater choice and advantage depending on the particular situation for which the wristband is needed. With respect to the first embodiments mentioned herein, as explained above, the inventor has conceived of arranging the form so that the cinch slot is outboard of the label portion, on a tab, and has eliminated the medical indicia thereby making the form more streamlined and suitable for use in a wider range of applications. Several arrangements for the label portion are shown and provide a variety of choices to suit different applications depending on the number of labels needed, and all without sacrificing the integrity of the form. As in other embodiments, bar coding or other means of identifying or numbering or segregating the forms may be used, limited only by the imagination of the form designer or user. Furthermore, the wristband form may have an imprint area available, such as for example imprinting a company name.

With respect to the second general category of wristband forms, the inventor has provided a tab at an end adjacent the face stock area, with the tab having a second slot surrounded by adhesive and through which the tail or free end portion is inserted for joining the wristband about the person wearing it. After the free end is inserted, the slot is preferable folded over about a fold line, and the free end is captured and adhered in place. The remaining free end may then be inserted through the second slot and hidden beneath the face stock out of the way and less likely to be caught on something. This arrangement allows for the extra free end to be kept intact so that the wristband may later be re-adjusted in length by merely lifting the folded over tab and withdrawing the free end for re-positioning. As an added feature, the face stock is preferably extended to the edge of the outboard slot to thereby cover over the adhesive closest to where the free end slides through, thereby making it less likely to "hang up" on adhesive as the wristband is applied. Furthermore, as the adhesive is applied to the area surrounding the second slot, it need not be applied as a patch on the tip of the free end as in other embodiments disclosed in the parent applications. Thus, as the free end is inserted through the slot, there is no patch of adhesive to inadvertently grab a patient's skin or body hair again making this embodiment less likely to "hang up" on the patient as it is applied. Instead, the adhesive is placed on a surface facing away from the patient.

In still other embodiments, slots are provided on each side of the face stock and through both of which the free end may be inserted. In this arrangement the face stock area overlies the free end, and the face stock area becomes less "rounded" than in other embodiments where only a single slot is used. This aids in reading the information placed on the face stock, and can be important in aiding this information should it be bar coded information. Also, with the two slot embodiment, the same form may be applied in different ways which enhances its versatility. This may be especially important for those applications where a single form may be intended to be used on different body parts of a patient. One such example is the Neo-natal, Intensive Care Unit (NICU) where wristbands are desirably applied not only to the leg but also the arm. In this application, the same wristband will be applied to different parts of the body, the leg and arm, and depending on size either one slot or both slots may be used to allow for patient comfort and ready accessibility to the imprinted information. However, even with the need to accommodate differently sized arms and legs, the same form may be used thereby minimizing inventory requirements and eliminating the waste or extra cost of using more than one sheet of wristbands.

While the principal advantages and features of the present invention have been explained above, a fuller understanding of the invention in all of its various embodiments may be attained by referring to the drawings and description of the preferred embodiments below.

DETAILED DESCRIPTION OF THE PREFERRED EMBODIMENT

Figure 1:
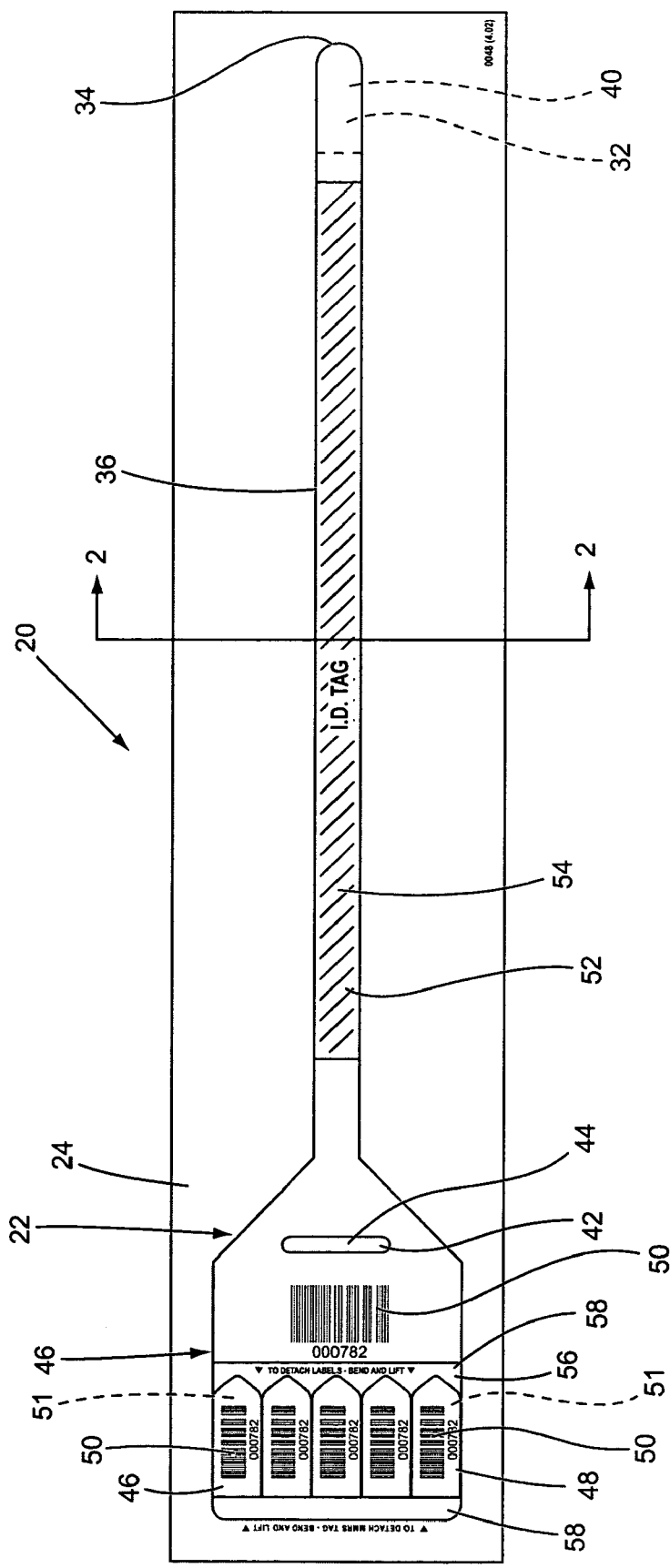
FIG. 1 depicts a top view of the first embodiment of the business form of the parent invention prior to the wristband/label assembly being separated from the carrier.
Figure 2:
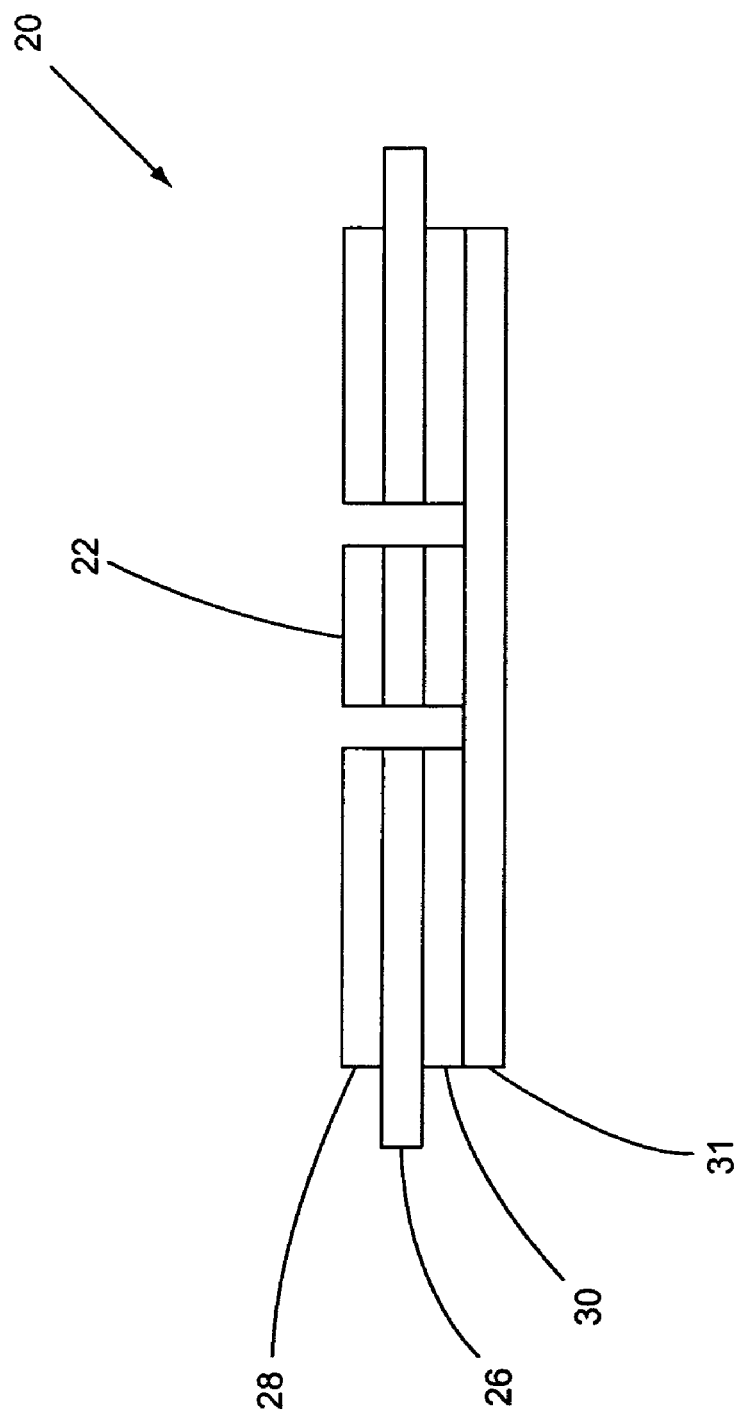
FIG. 2 is a side view of the first embodiment as shown in FIG. 1.
Figure 3:
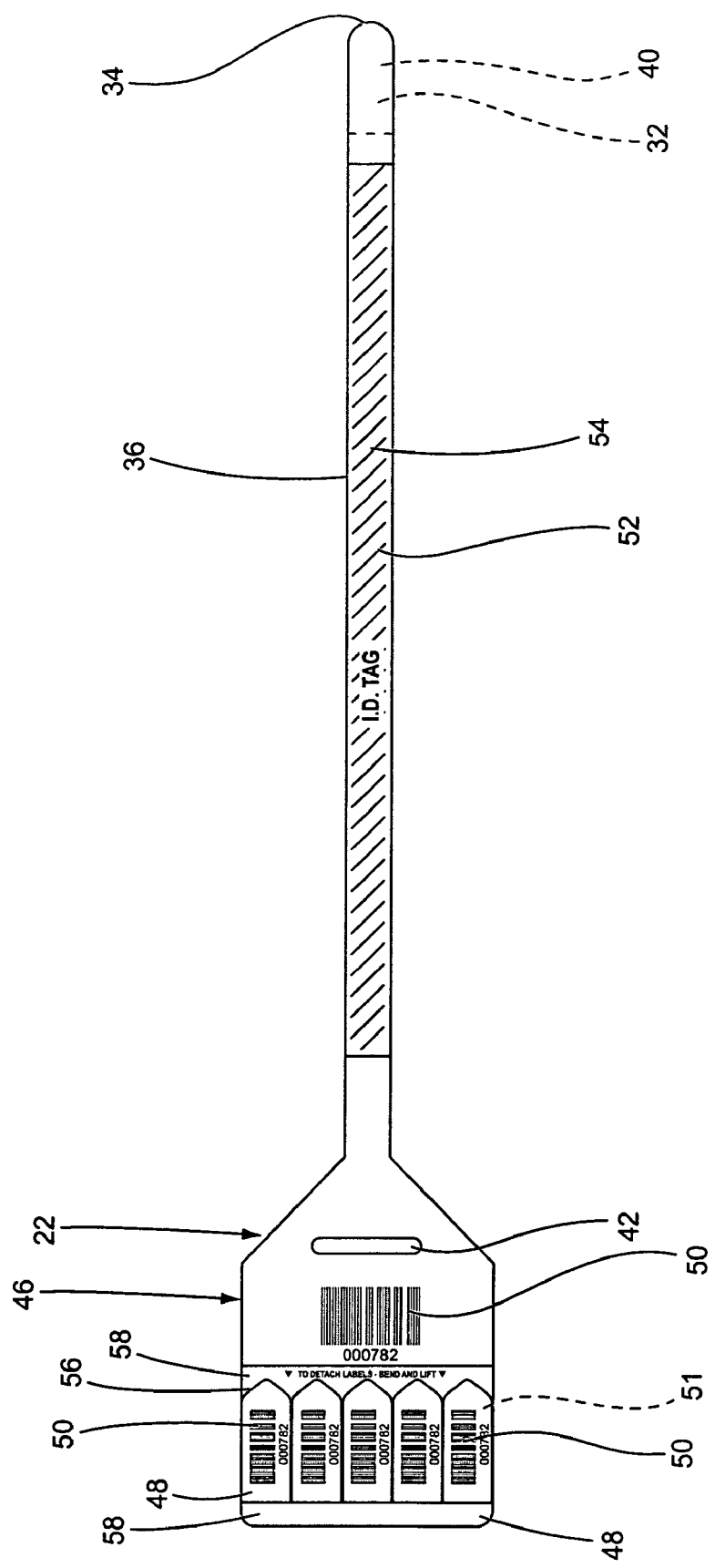
FIG. 3 is a top view of the wristband/label assembly after separation from the carrier of the first embodiment.

As shown in FIGS. 1–3, the first embodiment of the business form 20 of the parent invention generally includes a wristband/label assembly 22 die cut into a carrier 24 making an overall size of preferably approximately three and a half inches by seventeen inches, (3½"×17"). Generally, the business form 20 is assembled with a three web construction, with a poly laminated paper center web 26 sandwiched between a pair 28, 30 of thin film poly, transparent webs, and this is then dry adhered to a carrier web 31. The poly coated paper web 26 is dry adhered to the carrier web 31 so that it may be separated therefrom along its die cut to remove the wristband/label assembly 22 from the carrier 24. At an end of the form 20, an adhesive 32 is applied to the single end 34 of the wristband portion 36 of the wristband/label assembly 22. A separate patch 40, preferably made of paper with a release coating, covers the adhesive 32, with the webs die cut so that a portion of the patch 40 covering the adhesive 32 separates with the single wristband end 34 as it is separated from the carrier 24. A "cinch" comprising a slot 42 is formed when the wristband/label assembly 22 is separated from the carrier 24 as a filler 44 remains adhered to the bottom web 30.

The wristband/label assembly 22 of the first embodiment of the parent includes a wristband portion 36 and a tab portion 46. The tab portion 46 preferably includes a label portion 56 having a plurality of individual labels 48, each of which along with the body of the tab portion 46 are identified with an identifying indicia 50, preferably a bar code. While five labels 48 are shown, it is apparent to those of skill in the art that a greater or lesser number of labels could be provided in keeping with the scope of the invention. A release layer 51 preferably underlies the labels 48 and facilitates their removal from the tab portion 46 with a layer of adhesive being carried with each label for adhering the label to any other medium, such as a chart, a tag attached to a bag of belongings such as clothes, a medicine container, etc. Preferably, the wristband portion 36 also is color coded, such as with a coloring 52 along strap portion 54 of the wristband. While any convenient color scheme as known in the art may be utilized, one such convenient scheme is to use black for deceased, red for alive and needing immediate attention for survival, yellow for alive and needing attention for recovery, and green for alive and needing attention for non-life threatening injury. Other color schemes would be apparent to those of ordinary skill, and those color schemes are within the scope of the present invention. The tab portion 46 is separated from the label portion 56 by a die cut, thereby allowing for separation of the labels from the wristband portion, should that be desired, but being retained unless intentionally detached. Each of the labels 48 is defined by a die cut, and has a layer of adhesive and an underlying release layer for easy separation of each label 48 individually from the tab portion 46. Surrounding border members 58 may be peeled away from around the labels 48 to make it easier for them to be removed, such as when medical personnel have gloved hands or in the presence of fluids.

Figure 4:
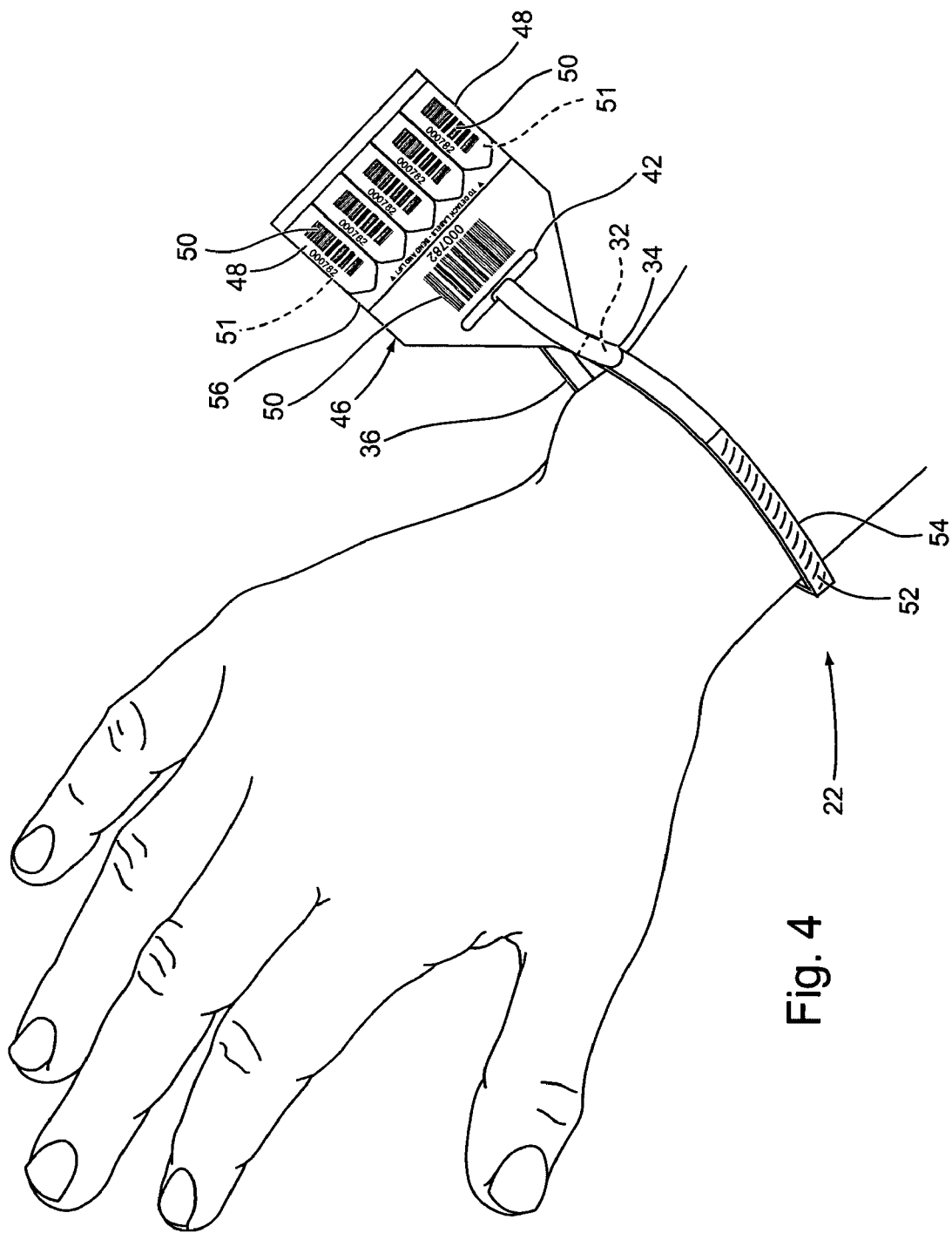
FIG. 4 is a view of the wristband/label assembly applied to a victim's appendage.

As shown in FIG. 4, the wristband/label assembly may be readily applied to a victim, such as around his wrist, by separating it from the carrier, looping the strap portion around the wrist and through the cinch or slot, pulling the strap portion tight as desired, removing the covering over the adhesive applied at the single end of the strap portion, and then affixing the single end to the strap portion to complete the circle or wristband. In this manner, a victim has been color coded as to medical condition, identified with an identifying indicia such as a bar code, and a set of labels have been made immediately available to mark any other items desired to be associated with the victim such as his possessions, his medical charts, medicines being administered, or any other item as desired.

Figure 6:
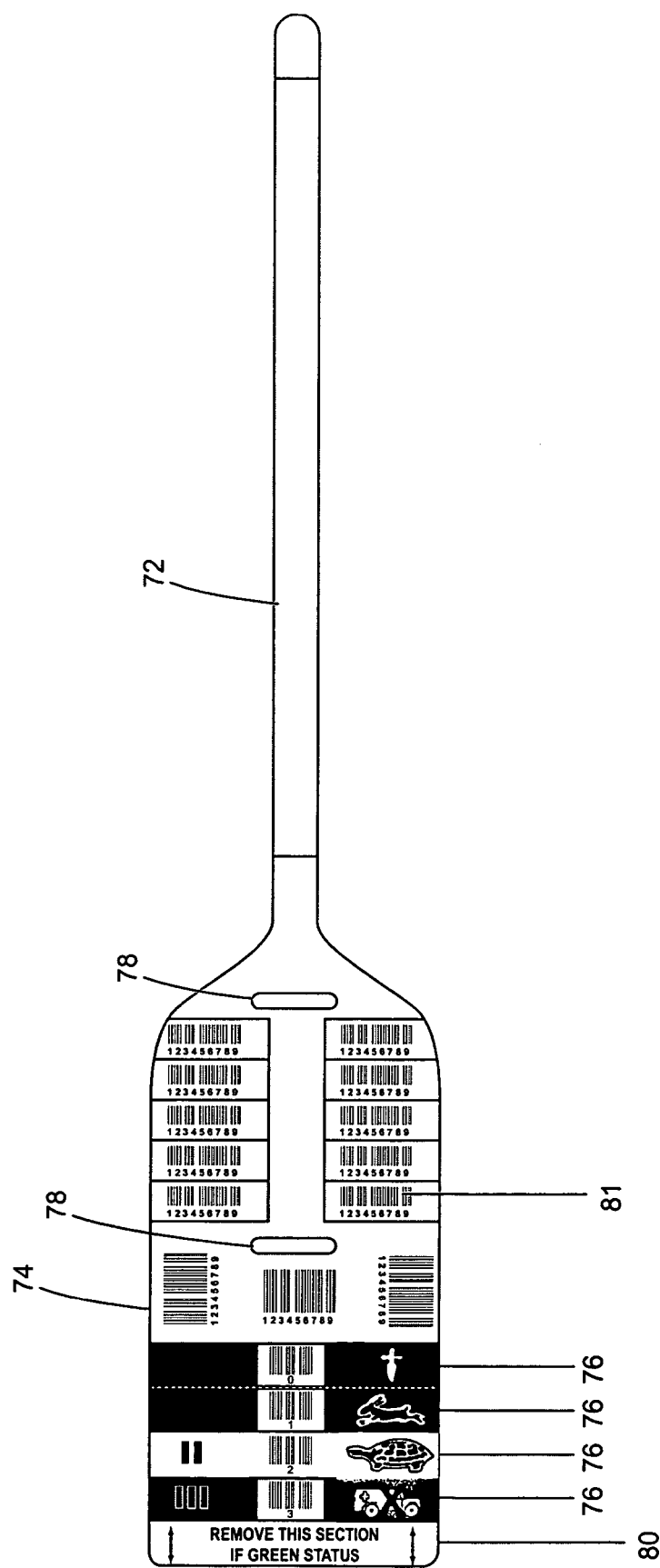
FIG. 6 is a top view of the second embodiment of the business form of the parent invention.
Figure 7:
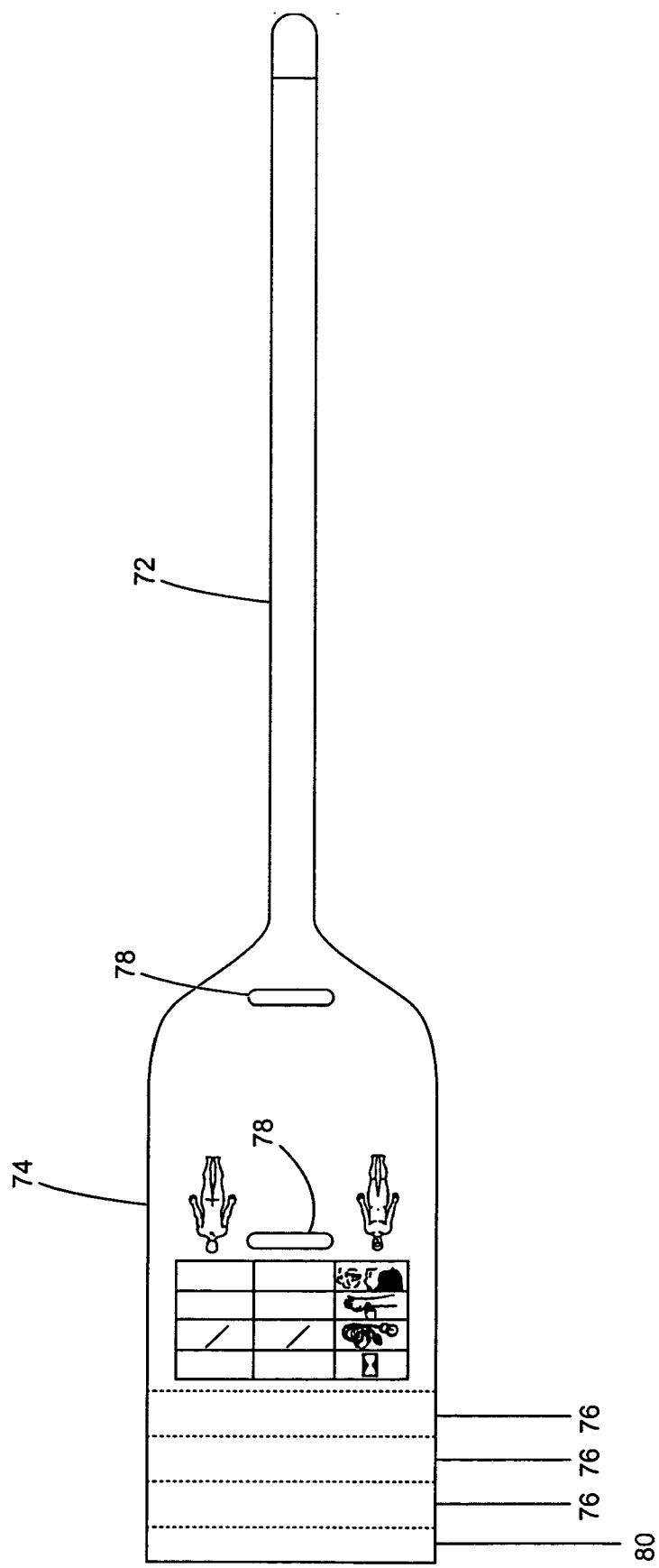
FIG. 7 is a bottom view of the second embodiment.
Figure 8:
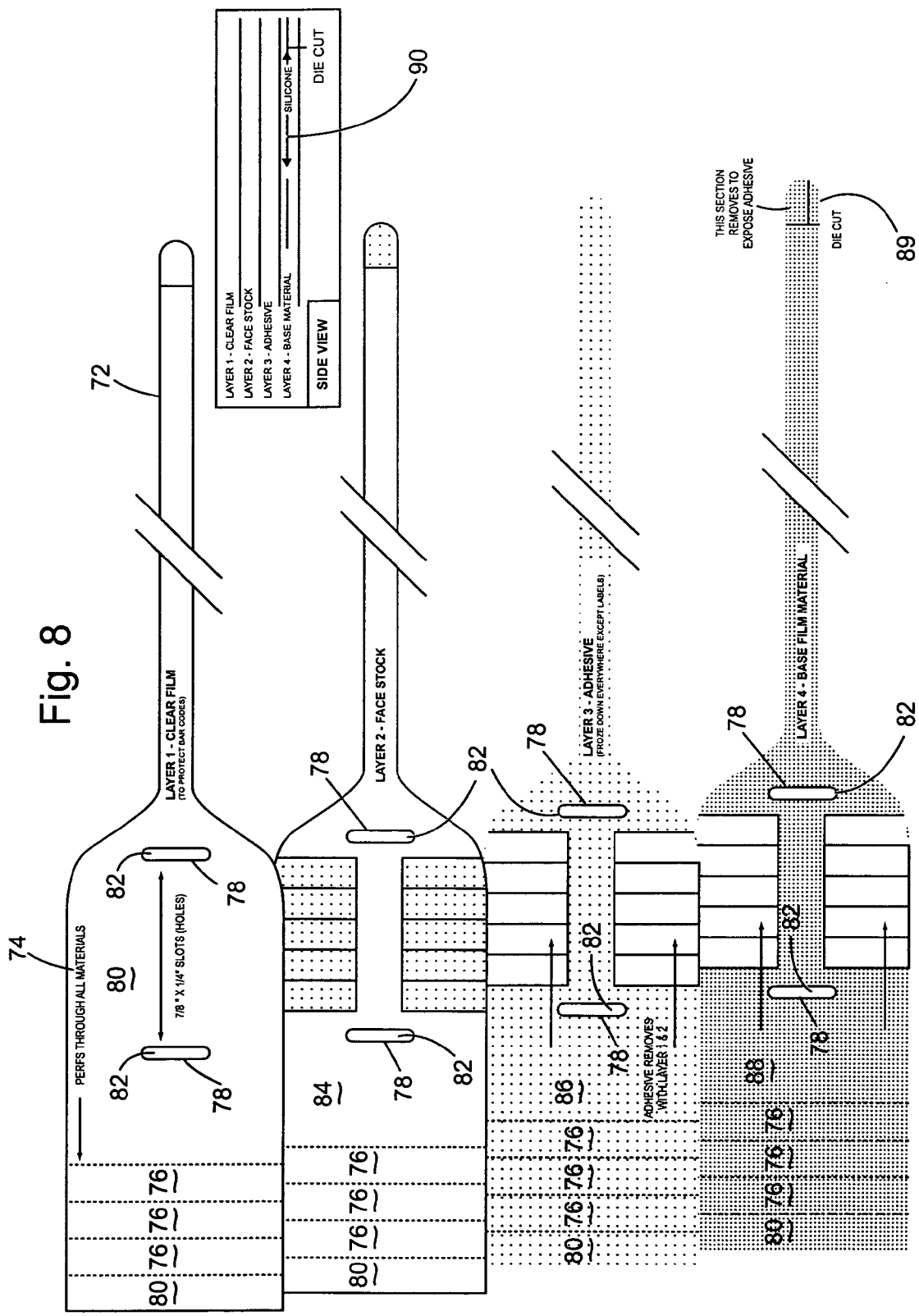
FIG. 8 is an expanded view of the second embodiment, detailing the four layers comprising the second embodiment.

The second embodiment of parent is shown in FIGS. 6–8, and is very similar to the first embodiment except that it is not supplied as part of a sheet type construction from which it must be separated prior to use, is pre-printed, has a different arrangement for indicating medical condition, etc. As shown therein, the second embodiment is completely formed and ready for use without first being separated from a carrier, as with the first embodiment. However, it also has a strap portion 72 and a tab portion 74. While the strap portion may also be color coded, it is preferred that a plurality of separable tabs 76 be provided, along with a dummy tab 80, for separation from the tab portion 74 so that an observer of the applied form may be assured that a conscious effort has been made to indicate medical condition. Otherwise, the dummy tab 80 is present indicating that this feature has not be used, at least as of yet. In addition to color coding, a bar code is also preferably indicated on the individual tabs 76 with each tab 76 having a matching bar code so that the victim's condition may be also scanned into the computer or data base at the same time as the patient's ID bar code. Further information may also be provided on the tabs 76, such as definitional information to instruct a medical technician as to the specific meaning to the various categories to help ensure consistency in marking victims despite the use of multiple and even untrained personnel. This information helps to make the present form almost self teaching as one never knows the quality or training of personnel who will be available when a medical emergency occurs. As shown in FIG. 7, the back of the tab portion 74 may also have additional instructing information, or a place for recordal of vital signs or other medical information such as allergies to medicine or the like. Of further note, as shown in this second embodiment is not one but two cinches 78, comprising slots. This allows the strap portion 72 to be sized more closely to varying dimensions and thus used with a wider variety of appendages. Other similar features are also included such as the bar code labels 81, shown arranged in two columns between the cinch slots 78.

FIG. 8 depicts the four layers used to form the second embodiment, as preferred. The top layer is a web 80 of a clear protective film extending across the entirety of the form, and perforated as noted to allow for the tearing off of tabs 76, 80, and with holes 82 forming the cinch 78. The second layer is comprised of a face stock 84, preferably pre-printed with information as desired with the majority of information contained in the form. The next layer is an adhesive layer 86, preferably a patterned layer and release coating as known in the art as shown, which allows for the removal of tabs 86 with a layer of self adhesive for applying the bar code on ancillary items, as explained in greater detail below. The bottom layer is a web 88 of a base film material which acts to protect the bottom of the face stock web 80. As is noted in the Figures, a patch 89 similar to patch 40 of the first embodiment is shown and which is used to attach the end of strap portion 72 and complete the wristband about the victim's appendage. More particularly, two sections of silicone 90 are shown in a side view inset in FIG. 8, with those sections of silicone lining up with the patch 89 and the bar code labels 81 so that upon separation they carry with them the layer of adhesive making them self adhering.

Figure 5:
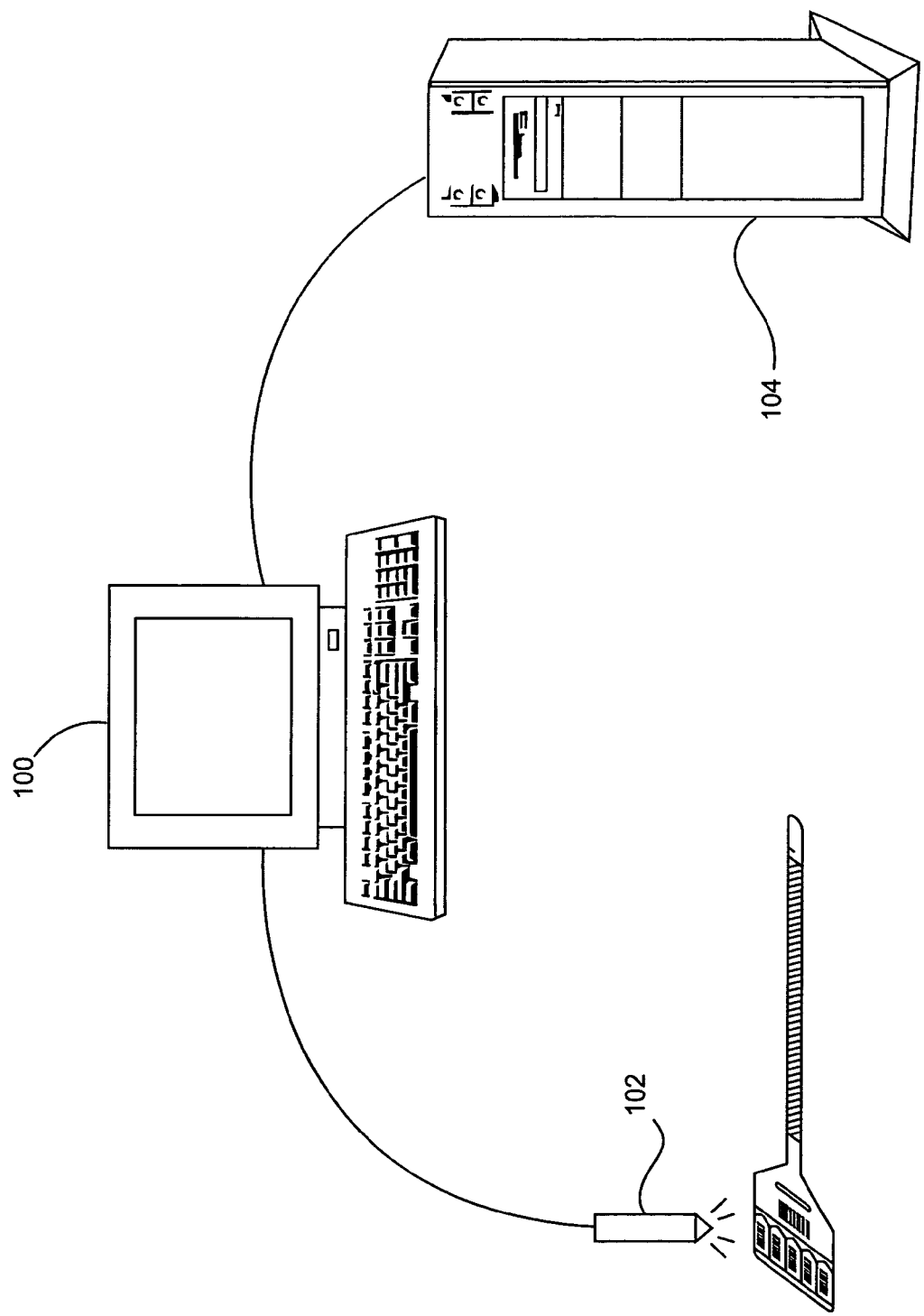
FIG. 5 is a diagram of the computer system used to implement the method of collecting and displaying over the internet the victim data.

As shown in FIG. 5, as the victims are processed, the parent invention also contemplates that this information may be input to a computer 100, the bar code being read in with a bar code swiper 102 or the like for preferably both of patient ID and medical condition, and then this information may be transmitted over the internet to a server 104 for collating and display at a web site. Multiple computers 102 could be readily connected to the same server 104, as is known in the art, and handle the input from a number of medical facilities at the same time. This permits this information to be made available almost immediately as victims are processed, through the web and at remote locations, eliminating the anxiety of family members who physically search for their relatives or loved ones.

While the principal advantages and features of the parent invention have been illustrated through an explanation of its preferred embodiment, there are other aspects and variations of the parent invention as would be apparent to those of skill in the art. For example, rather than bar coding, other identifying indicia could be used on the form. The form could be used in other applications other than in emergency situations in the field. Rather than color coding, other coding or indicators could be used to sort victims, or they could be sorted into other categories according to differing medical categories, or coding could be dropped from the form, as desired. Other construction could be used for the form, including especially the wristband portion, such as self laminating construction and the wristband would still be protected from damage during its single use. Other means could be used to attach the wristband rather than looping a single end around and through a slot. Another form of a cinch could be used, or a different arrangement of the cinch. Still other variations would be apparent to those of skill in the art, and the parent invention is intended to be limited solely by the scope of the claims appended hereto, and their legal equivalents.

Figure 9:
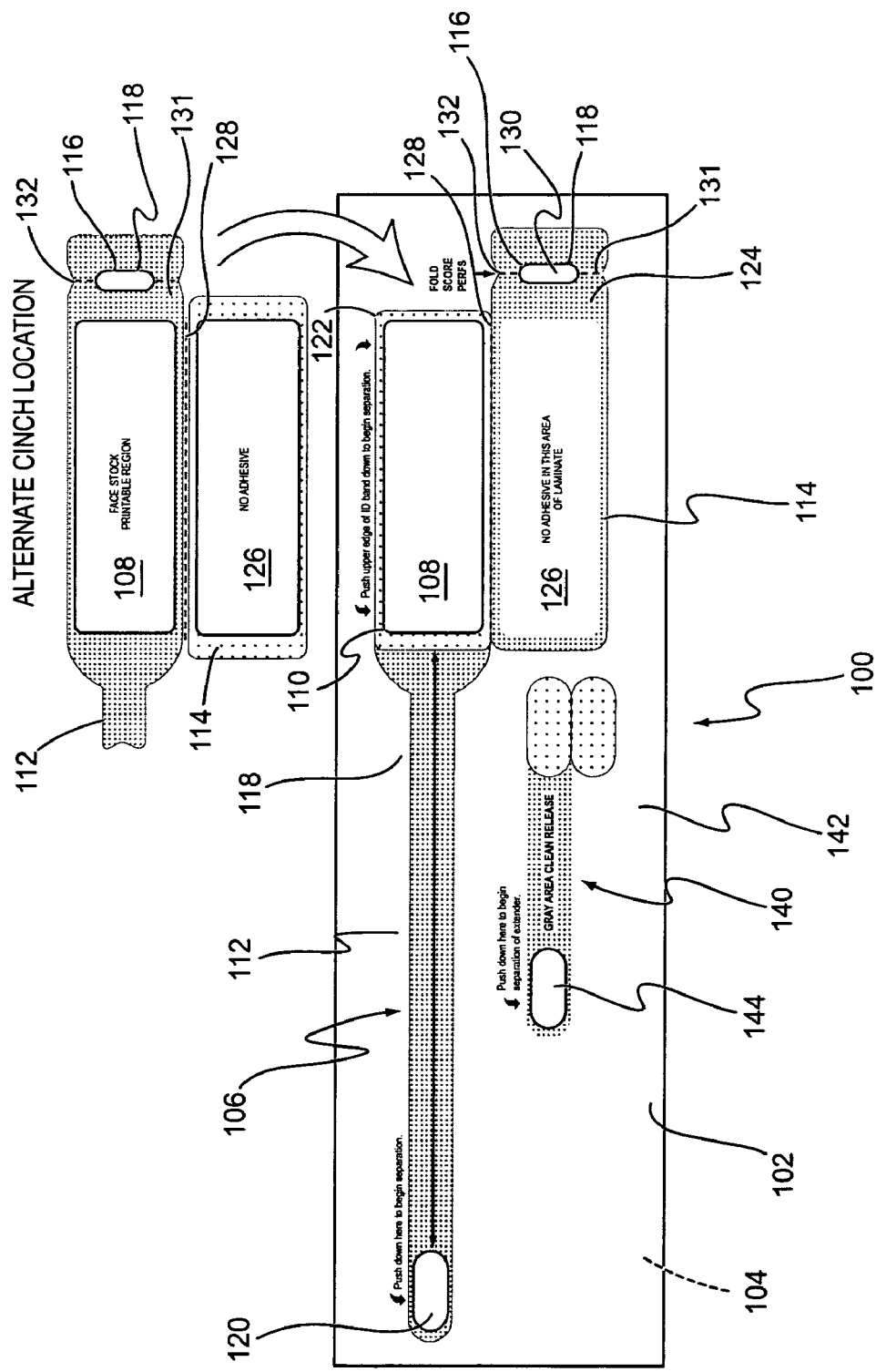
FIG. 9 is a top view of the first embodiment of the self laminating wristband with an inset depicting an alternate location for the cinch, and an extender formed in an approximately envelope size sheetlet.

The invention 100 of the second parent invention is shown in FIG. 9 and is depicted therein as formed in a two layer, sheetlet sized construction of about 3 inches by 11 inches. The top layer 102 is preferably a face stock, such as bond or the like as would readily accept a printed image from a laser printer or other computer controlled printer, and a bottom laminate layer 104 which underlies the face stock layer 102 and is joined by a patterned adhesive layer including portions which are release coated, as will become apparent upon further reading. The invention 100 generally comprises a self laminating wristband 106 having a printable region 108 of face stock defined by a die cut 110 therein, and an integrally formed strap portion 112, laminating portion 114, and cinch 116 similarly formed by a die cut 118 in the laminate layer 104. A patch of face stock 120 is also die cut into the face stock layer 102, and covers a patch of adhesive with which the strap portion is adhered as the wristband 106 is applied to a patient, as will be explained. The length of strap portion 112 is covered by a release coating so that after it is removed from the sheetlet 100 it does not carry any adhesive with it. The laminating portion 114 has a layer of adhesive between a top portion thereof 122 and the face stock region 108 to adhere it thereto. However, a bottom portion 124 of the laminating portion 114 has a window 126 of area where no adhesive is applied so that as the laminating portion is folded over there is no layer of adhesive covering the printable region 108. A fold or perf line 128 if formed between the laminating portion halves 122, 124 as an aid in forming the wristband 106 after it is separated from the sheetlet 100. The cinch 116 generally comprises a slot 130 formed in an extension 131 and aligned generally perpendicularly to the face stock region 108 and strap portion 112 for easy insertion of the strap portion 112 therethrough. There is also provided a fold or perf line 132 along the central axis of the slot 130 through the width of the extension 131, and adhesive covers the extension 131 so that the extension 131 may be folded over onto the strap portion 112 after it has been threaded through the slot 130 to its desired length. The extension 131 and cinch 116 are shown to be adjacent the bottom half 124 of laminating portion 114, which results in the adhesive layer of the extension 131 facing towards the patient's wrist as the wristband is applied. Alternatively, the extension 131 and cinch 116 may be formed adjacent the top half 122 of the laminating portion 114 as shown in the inset of FIG. 9 and with this construction the extension adhesive faces away from the patient as the wristband is applied. With this alternative arrangement, the wristband may lie flatter against the patient, as the other arrangement creates a small tab which may or may not lie flat depending on how tight the wristband is drawn. However, this is not considered significant.

In use, this wristband embodiment is first separated from the carrier sheetlet by pushing down on the end of the strap and/or the die cut face stock area 108, and peeling it away, thereby separating a matrix comprising the wristband assembly. The laminating portion 114 is then folded together to enclose the printed face stock region. The wristband is next applied to the patient's wrist by wrapping the strap about the wrist, inserting it through the cinch, folding over the extension to adhere it to the strap, and then exposing the adhesive on the end of the strap and adhering it back onto itself to secure the excess strap. The caregiver can choose the tightness of the wristband by threading more or less of the strap through the slot in the cinch before adhering the strap to the extension.

Also shown on the sheetlet 100 is an extender 140 generally comprising a clamshell joinder portion 142 at one end of a length of laminate layer 104 and a patch of face stock 144 covering a patch of adhesive at the other end. The extender 140 may be used to extend the effective length of strap portion 112 and is applied by adhering the clamshell portion 142 anywhere along the length of strap portion 112 and using the patch of adhesive on the extender 140 to join the strap portion 112 to itself as just described. The length of extender 140 is adhesive free, as the strap portion 112, so that no adhesive is exposed to the patient's skin.

Figure 10:
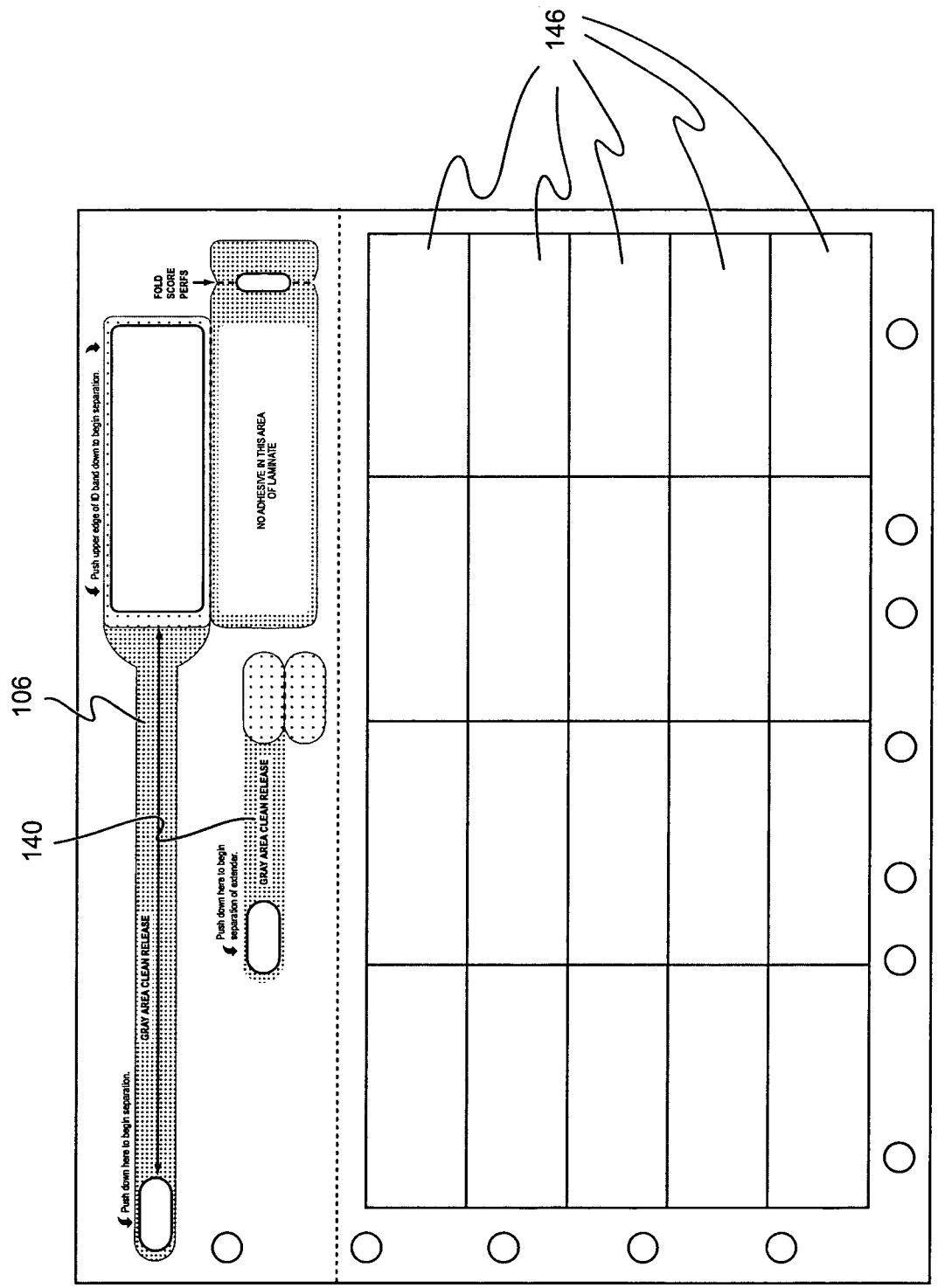
FIG. 10 is a top view of the first embodiment of the self laminating wristband and extender formed in a page sized sheet with a plurality of self adhering labels.

As shown in FIG. 10, the wristband 106 and extender 140 may be included as part of a page sized sheet along with a plurality of self adhered labels 146. As with previous inventions shown in the inventor's prior patents, it has been found to be desirable to print identifying information relating to a patient not only on a wristband but also on labels which may then be separately peeled off as needed to label items dedicated for use by the patient or to identify other medical items such as blood samples, tissue samples, etc. Thus there has found to be a need for the present invention configured as shown in FIG. 10.

Figure 11:
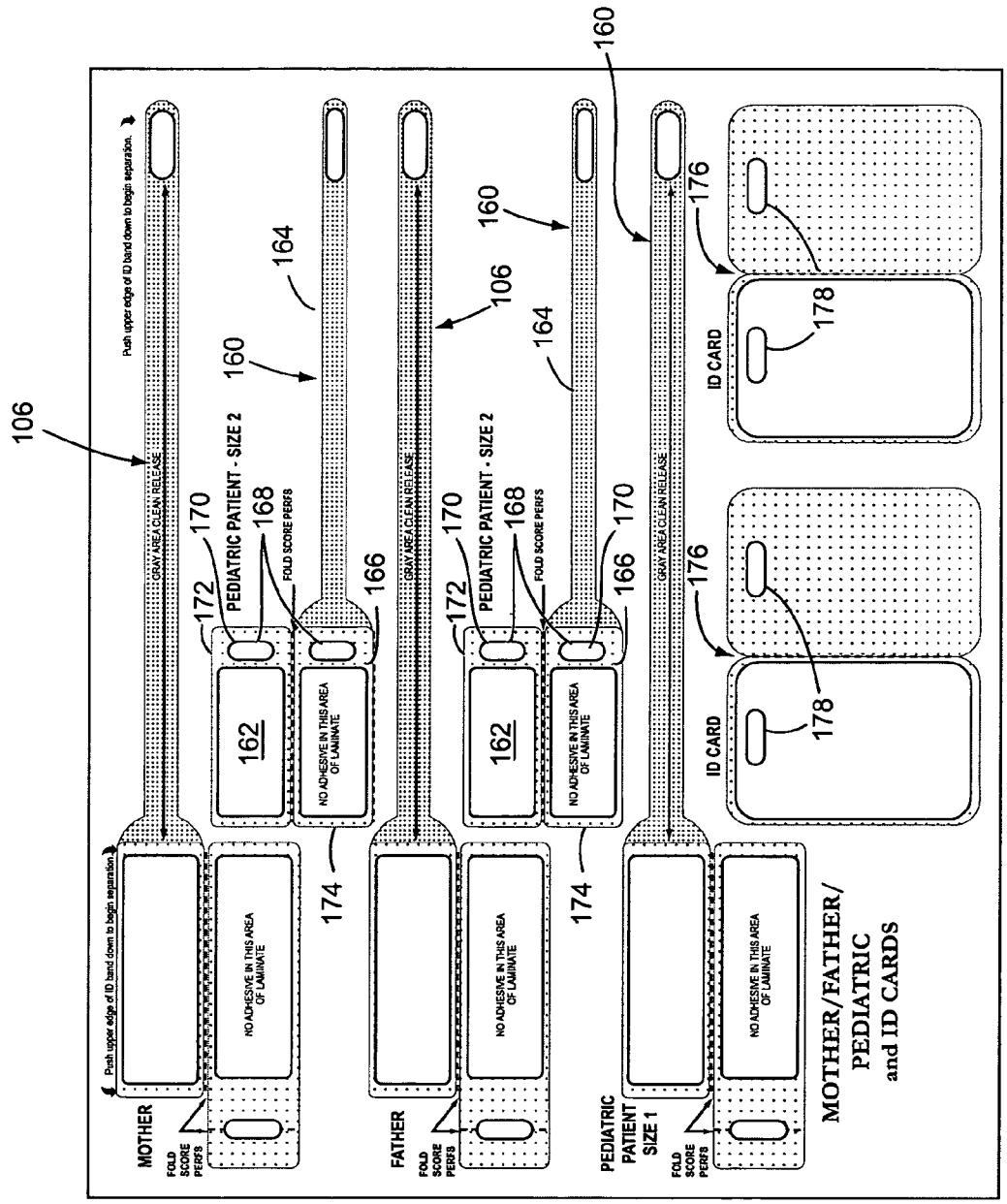
FIG. 11 is a top view of a page sized sheet having a plurality of self laminating wristbands of varying lengths, and depicting an alternate construction for the wristband, coupled with a pair of ID cards.

As shown in FIG. 11, a page sized form may also be provided with a mix of wristbands 106 as well as a different embodiment of wristband 160, which is preferably somewhat smaller in length than wristband 106, and which has a slightly different arrangement for the cinch. As shown therein, there are two wristbands 160, each of which has a printable face stock region 162 die cut from the face stock layer as with wristband 106. And, a strap portion 164, laminating portion 166 and cinch portion 168 are also die cut into the laminate layer, as with wristband 106. However, cinch portion 168 comprises a pair of slots 170 die cut adjacent both of the top half 172 and bottom half 174 of laminating portion 166, so that as the two halves 172, 174 are folded over to laminate faces stock region 162, the slots 170 are aligned to overlie each other and create a single opening intermediate the face stock region 162 and strap portion 164. With the cinch located in this position, several differences are noticeable. First, the wristband 160 may conveniently circumscribe a smaller circumference so that it may readily fit onto a smaller wrist, such as a baby's, as it takes the face stock region 162 and laminating portion 166 out of the loop forming the wristband. Instead, the face stock region 162 and laminating portion 166 form into a "hang tag" which essentially hangs from the strap portion 164 after the wristband 160 is applied to a patient. Note that the strap portion 164 extends from the bottom half 174 in this embodiment instead of from the top half 172 as in the first embodiment, thereby allowing the strap portion 164 to wrap around and through the cinch portion 168 and then back onto itself without passing over or obscuring the face stock region 162. Although this wristband 160 construction is shown as being adapted for smaller wrists, it may also be used with a longer strap portion 164, or with an extender 140, and may be viewed as a matter of design choice. Also shown on the sheet are a pair of ID cards 176, that are themselves self laminating, with a slot 178 for convenient attachment directly to either of the wristbands 106, 160, or separately to a clip or for being carried in a user's wallet. This assemblage of wristbands and ID cards has been found to be especially useful for pediatric situations with a wristband for each parent, an ID card for each parent, and two smaller wristbands for one or two babies or children.

Figure 12:
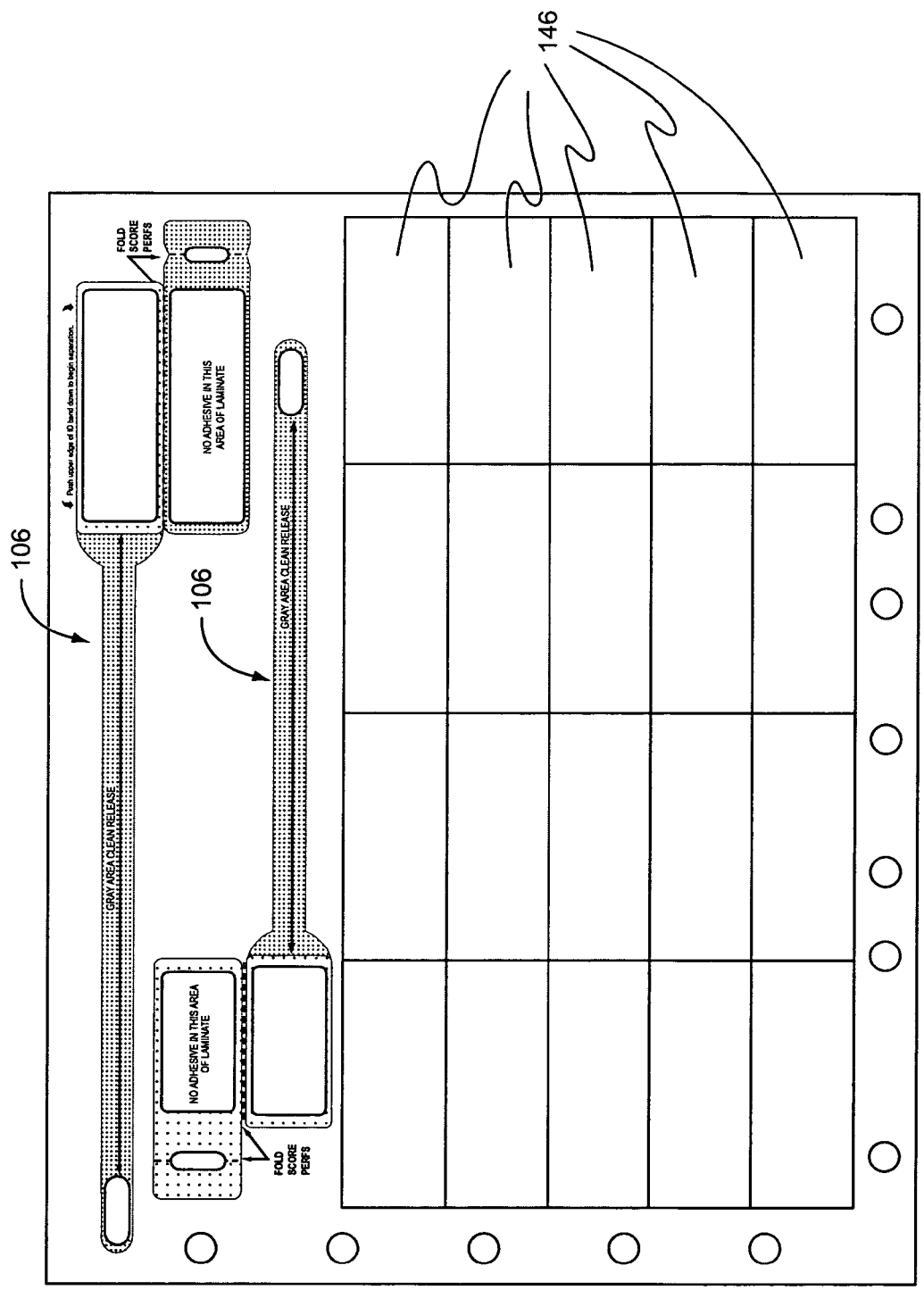
FIG. 12 is a top view of a page sized sheet having a pair of wristbands and a plurality of self adhering labels.
Figure 13:
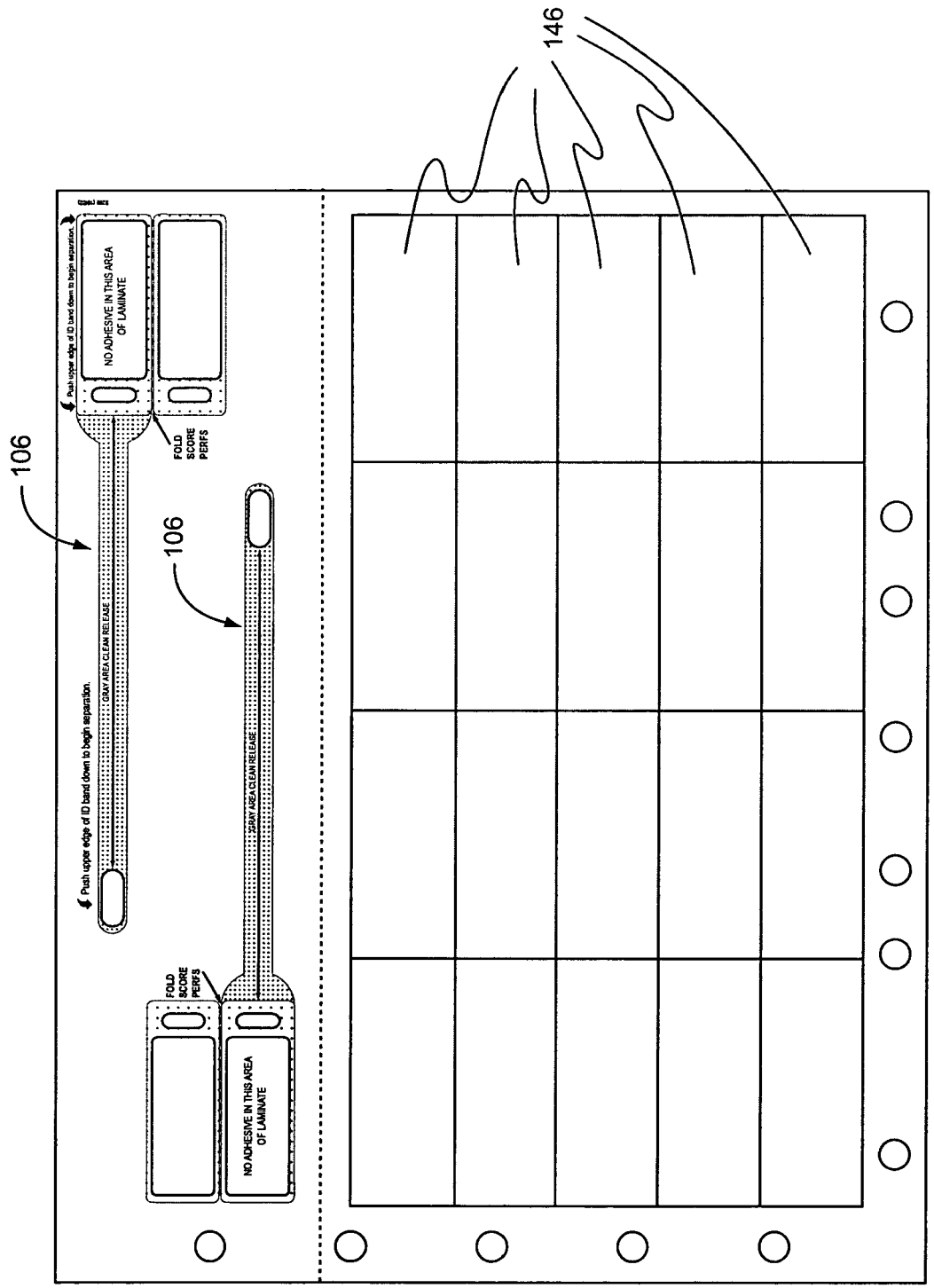
FIG. 13 is a top view of a page sized sheet having a pair of wristbands of alternate construction and a plurality of self adhering labels.

FIG. 12 depicts a sheet sized form containing two wristbands 106 along with a plurality of self adhering labels 146 which is a slightly different configuration than that shown in FIG. 10, but with the same inventive wristbands being used. FIG. 13 depicts a sheet sized form similar to that shown in FIG. 12 except that an alternative wristband 160 is used. While the inventor has found that these particular groupings of products have met with acceptance and commercial success for particular applications, other combinations of wristbands, of different construction, with or without labels or ID cards, may be found desirable as a matter of design choice.

Figures 14, 15:
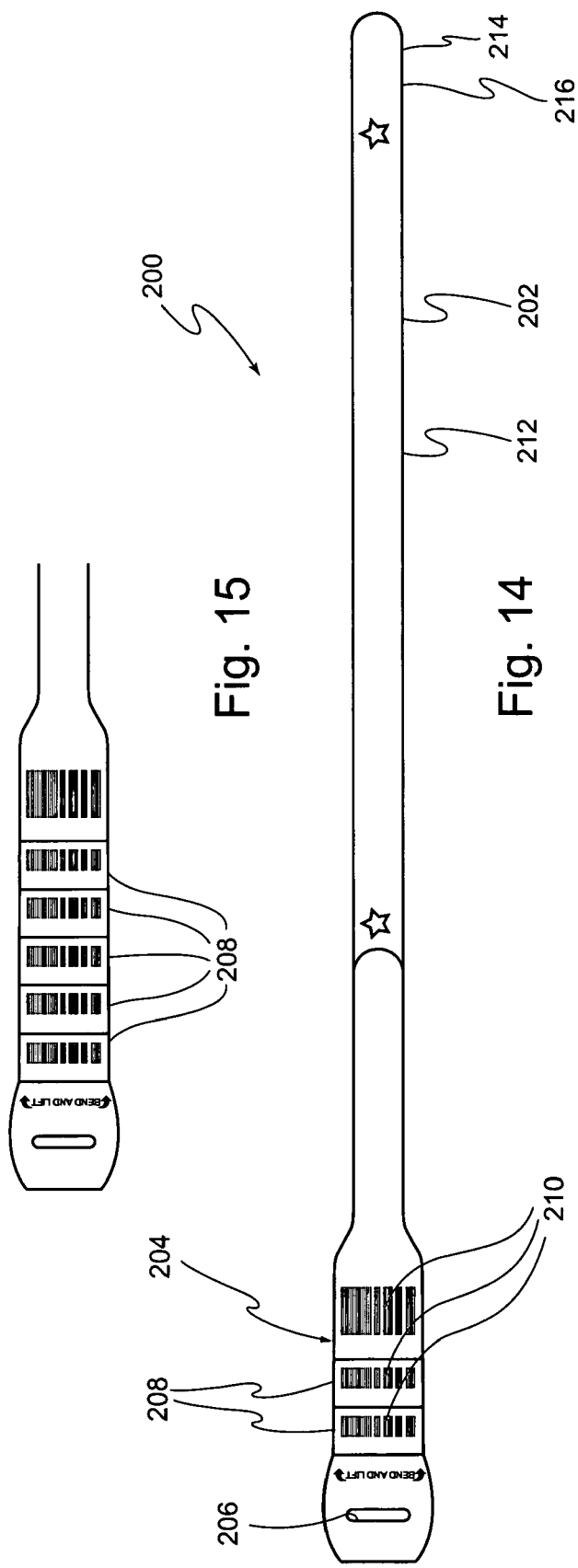
FIG. 14 is a top view of a wristband/label form with the cinch slot outboard of two, full width labels contained in the tab.
FIG. 15 is a top view of a variation of the embodiment of FIG. 14 except that more full width labels are contained in the tab.

FIG. 14 depicts the present invention which represents the continuing inventive efforts of the inventor herein. As shown therein, a wristband 200 has a strap portion 202 and a tab 204 which contains a cinch slot 206 and a pair of full width labels 208. Each of the labels 208 and the adjacent area of the strap portion 202 are encoded with identifying indicia 210, shown as preferably bar coding. An imprint area 212 is included on the strap portion 202 which may be imprinted with any desired identifier such as the company or hospital name, or other message or the like. The construction of this invention may be similar to that described above, with a multi-web arrangement as described for the embodiment of FIG. 1. The labels may be removed and applied to any other associated materials, depending on the use made of the wristband. In a medical setting, the labels may be used for medical charts, medicines, eating utensils, clothing bags, or any other commonly known need. In other applications, other uses may be made, such as for personal items, tickets, receipts, charge identifiers such as for a credit card charge, etc., as limited only by the imagination of the user.

The embodiment shown in FIG. 14 has a generally slender strap portion 202 which may be more comfortable for a person to wear about his wrist, and the cinch slot 206 may be slightly wider than the width of the strap portion 202 to facilitate its insertion as the wristband 200 is secured. A protective patch 214 of may conveniently cover a patch 216 of adhesive at the tip of the strap portion 202 until it is desired to apply the wristband 200 to a person. After insertion through the cinch slot 206, the patch 214 may be removed and the strap portion 202 folded over and adhered onto itself to complete the application process. The strap portion 202 may be tightened about the person by pulling on it after it has been inserted so as to achieve a tight banding of the wristband about the person's appendage. Alternately, the strap portion 202 need not be tightened, and the wristband 200 left "loose" to provide a secure but perhaps more comfortable fit.

Figure 17:
FIG. 17 is a top view of yet another variation of the embodiment of FIG. 14 except that a pair of perpendicularly arranged labels are contained in the tab
Figure 16:
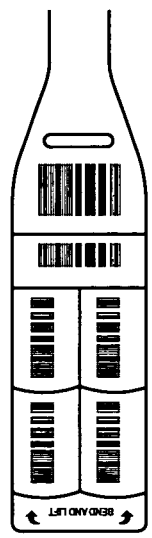
FIG. 16 is a top view of still another variation of the embodiment of FIG. 14 except that in addition to a full width label, several pairs of labels are arranged in perpendicular fashion in the tab.

Label variations of the basic arrangement shown in FIG. 14 are depicted in FIGS. 15–17. These include a plurality (5) of labels 208 all arranged in the same full width orientation as shown in FIG. 15, a single full width label and two pairs of perpendicularly arranged labels as shown in FIG. 16, and a single pair of perpendicularly arranged labels as shown in FIG. 17. While these label arrangements are shown as anticipated to most desirably meet the needs of intended users, it would be apparent to those of skill in the art that other label arrangements could be used without departing from the scope of the invention.

Figure 18:
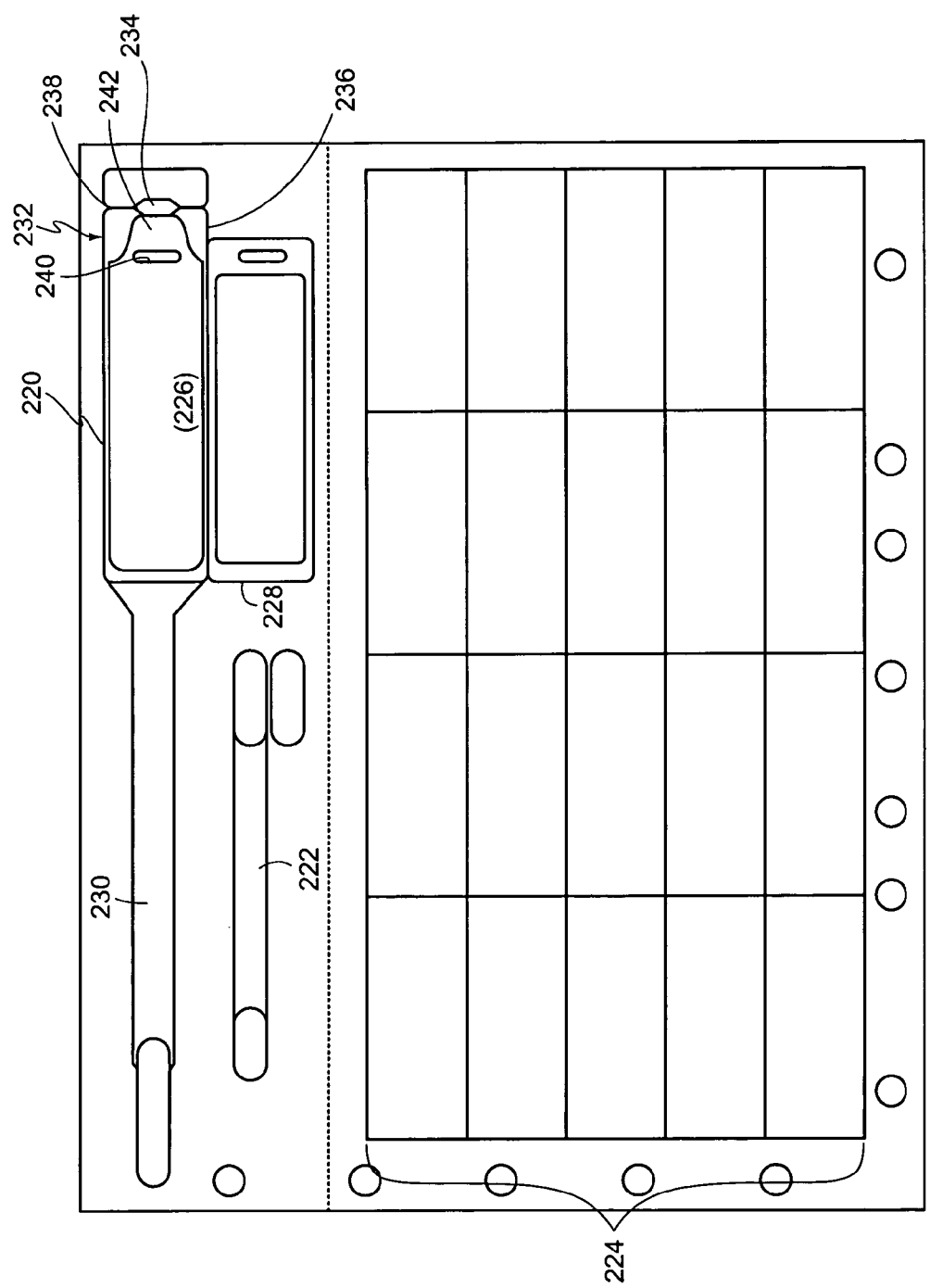
FIG. 18 is a top view of a page sized sheet having a wristband with outboard cinch slots, an extender and a matrix of labels.

Depicted in FIG. 18 is an approximately page sized sheet containing a self laminating wristband 220, an extender 222 and a plurality of self adhering labels 224. The various webs used in constructing this sheet have been explained above. The self laminating wristband 220 includes a face ply portion 226 preferably formed in the face stock layer, a lamination layer portion 228 preferably formed in the lamination layer, a strap portion 230 also preferably formed in the lamination layer, and an attachment portion 232 preferably formed in the lamination layer. As shown in FIG. 18, one slot 234 is formed in an extension part 236 of the attachment portion 232. A fold line 238 bisects the slot 234 as an aid in folding the slot 234 over to adhere the strap portion 230 as will be explained. As shown, the fold line 238 may comprise an incomplete cut at either side, through the central axis of the slot 234 and through the lamination layer. A layer of adhesive substantially surrounds slot 234 so that as it is folded over it adheres to the strap portion inserted therethrough. A second slot 240 may be formed in both of the face ply or stock portion 226 and in the underlying lamination layer. The face stock portion 226 has a tab 242 extending from the edge of the generally rectangularly shaped print or image area and up to the edge of the slot 234.

In use, the sheet may be first processed through a laser printer or the like to apply information to the labels 224 and the wristband 220, such as a patient's name, hospital admission number, or other information. The wristband may then be separated from the sheet and applied to a patient's wrist much as described above in connection with the other embodiments of the parent invention except that the strap end is inserted through slot 234 and then the tab is folded over to adhere the strap end in place. Adhesive need not be applied to the end of the strap as in other embodiments and instead the adhesive applied to the area substantially surrounding the tab slot secures the strap in place. It is noted that the face stock tab 242 shields the strap end from contacting a surface with adhesive and that unlike other embodiments there is no adhesive on the strap end which moves past the patient's wrist as the wristband is applied. This helps to ensure that the wristband doesn't become "fouled" as it is applied, making the wristband even more likely to be applied successfully to difficult or uncooperative patients. The extender 222 may be used as described with other embodiments to extend the effective length of the wristband 220, and the extender similarly need not have adhesive applied to its end.

Figure 19:
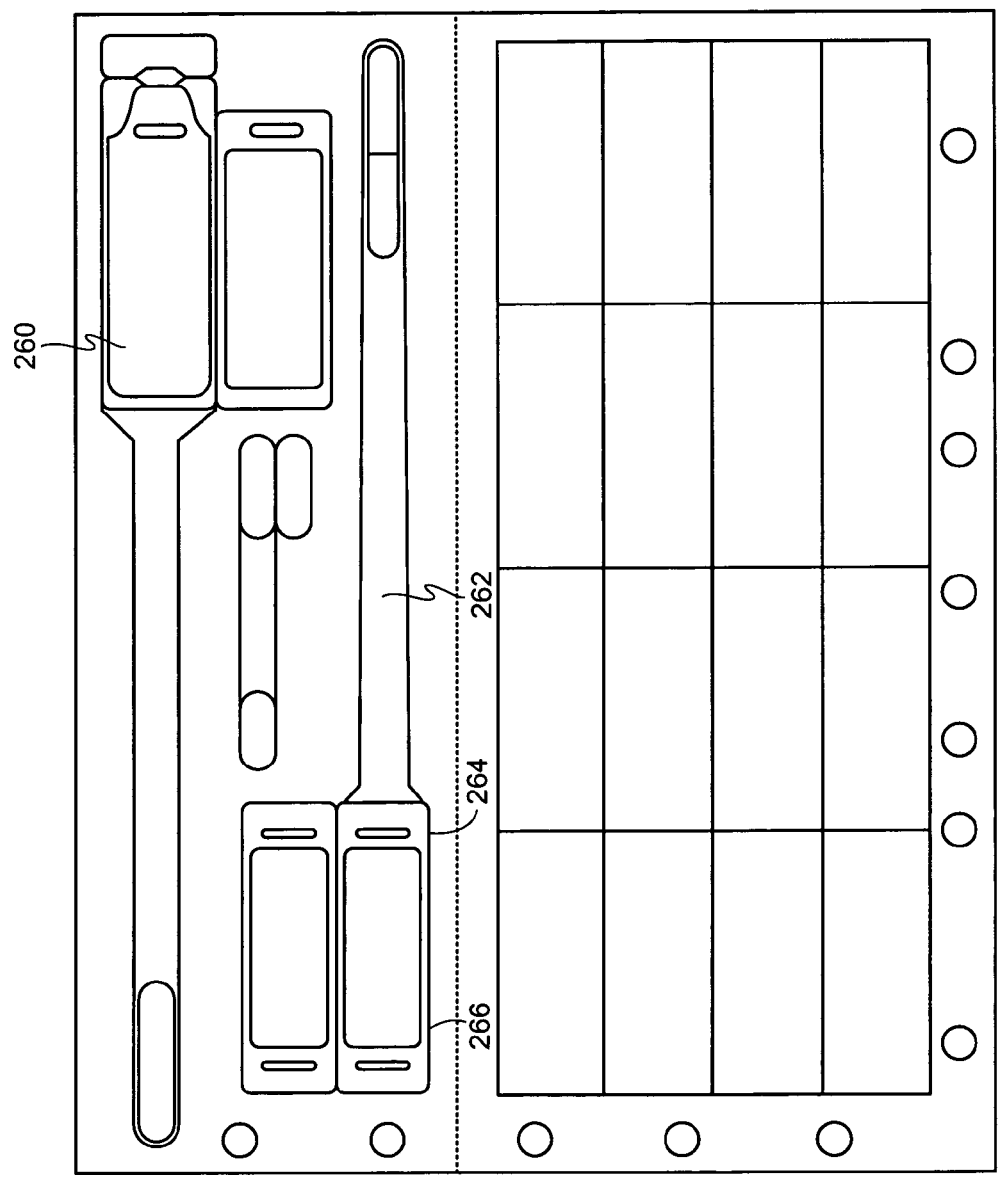
FIG. 19 is a top view of a page sized sheet having a pair of wristbands with one wristband having a pair of outboard cinch slots, another wristband having a cinch slot on either side of the face stock, an extender for use with either, and a matrix of labels.

FIG. 19 depicts another arrangement of wristbands and labels similar to that of FIG. 18 except that two wristbands are provided, of generally shorter length, and with a different slot arrangement for one of the wristbands. The wristband 260 shown near the top of the sheet is designed the same as the wristband 220 as shown in FIG. 18. As explained above, this wristband 260 is conveniently applied about a patient's wrist. The second wristband 262 has a cinch slot 264, 266 on either side of the face stock portion 268, and the strap end 270 has a patch of adhesive 272. In use the second wristband may be applied in several different orientations. One such orientation is for the strap end to be inserted through both slots 264, 266, passing underneath the face stock portion 268. In this orientation the face stock portion has a tendency to stay flatter after the wristband is applied and, with infants or small wrists or other tightly drawn wristbands, this flatter orientation aids in reading any bar coded information on the face stock. Another orientation is for the strap end to be inserted through the inboard cinch slot 264 so that the face stock portion 268 hangs freely from the wristband 260. Still another orientation is for the strap end to be inserted through the outboard cinch slot 266 which is very similar to that as described above for other embodiments. In this orientation, the wristband is at maximum length with the face stock portion 268 forming part of the wristband circle, and the strap end folded back onto itself for attachment. These two wristbands form a unique combination for application to pediatric cases as the different wristband constructions allow for wristbands to be applied to both arms and legs of infants, in different orientations, all with only one sheet being consumed.

Figure 20:
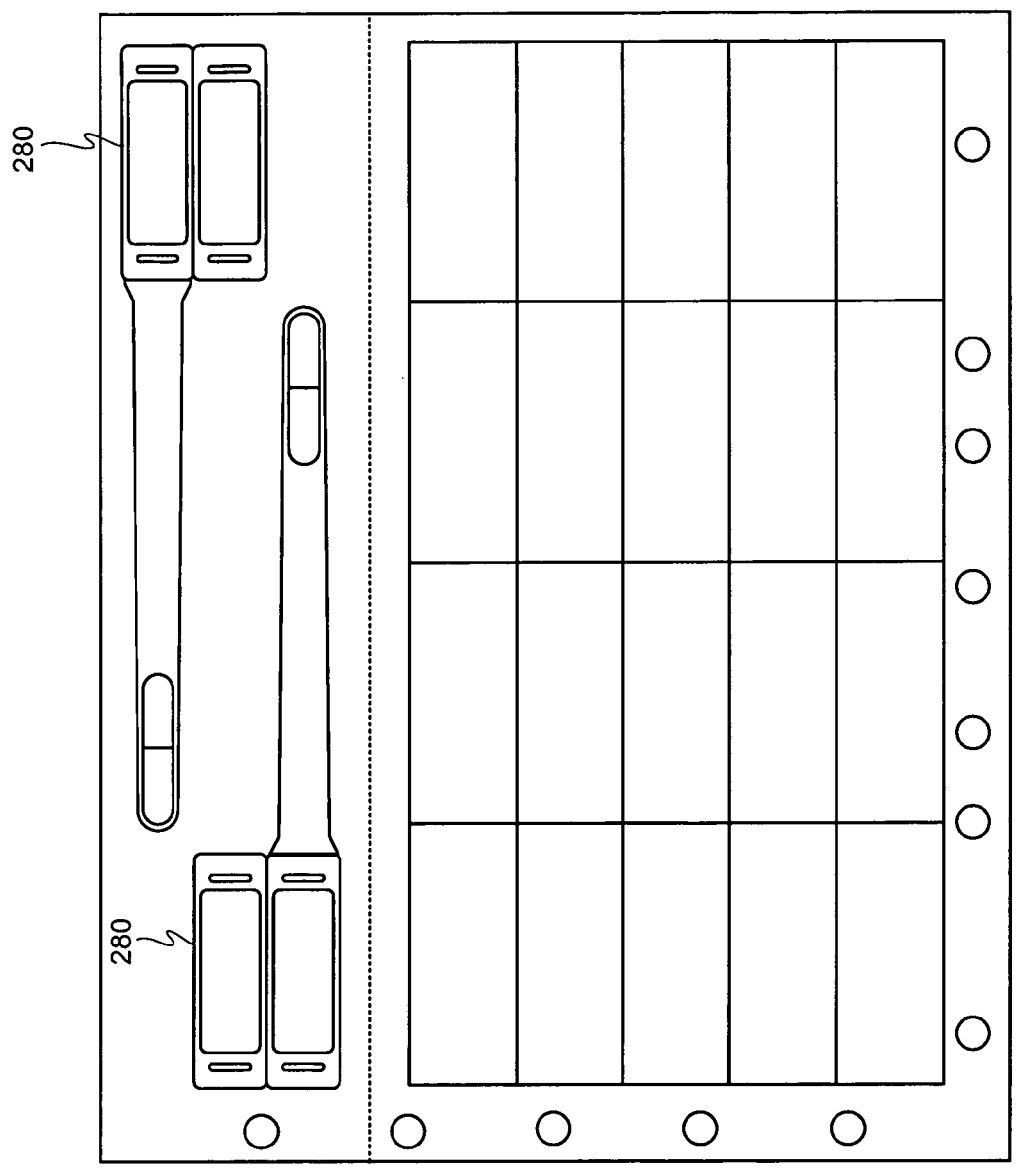
FIG. 20 is a top view of a page sized sheet having a pair of wristbands each having a cinch slot on either side of the face stock.

The sheet depicted in FIG. 20 provides two wristbands 280 along with a plurality of self adhering labels 282. In this embodiment the two wristbands 280 are of the same design as the wristband 262 as shown in FIG. 19. This arrangement is particularly adapted for use with neo-natal intensive care unit infants, as the two wristbands may both be arranged in either of two orientations, as explained above, which allows for maximum flexibility in applying two wristbands to either arms or legs of infants undergoing intensive care. In this situation, many different kinds of conditions are encountered and this flexibility allows for their successful use with consumption of a single wristband form and label set.

The inventions have been disclosed herein in several embodiments with several alternatives to the construction of the wristband, as well as other inventive features and accessories including an extender. It will be appreciated by those of ordinary skill in the art that various alternatives not specifically mentioned are well within the scope of the these inventions. Some of these alternatives include the choice of specific materials for each layer of face stock or laminate, the particular adhesive used, and other details of construction for the page sized sheet in which the wristband is formed. The particular length or shape of the strap may be varied to adapt to the particular application, the location of the patch of adhesive at the end of the strap may be changed or eliminated, the point at which the strap extends from the laminating portion, and other arrangement details may also be considered as part of the invention. While it is considered as desirable by the inventor to not laminate the strap portion, there is no reason why it need not be laminated. Face stock shape or size may be changed, and the tab extending to the outboard slot in several of the embodiments may be separated from the face stock, or pattern adhesive used to eliminate the adhesive adjacent that edge of the slot, and yet achieve a similar effect. The preferred embodiments disclosed herein are intended to be exemplary and not limiting as to the subject matter of the invention. Other similar, or different, changes will be contemplated and those changes are to be considered as part of this invention which should be limited only by the scope of the claims as appended hereto, and their legal equivalents.

What is claimed is:

1. A business form comprising a self-laminating wristband, said wristband having a printable face ply portion, a lamination layer portion for substantially surrounding the printable face ply portion, a strap portion formed in said lamination layer portion and extending from a single side of said face ply portion for wrapping about a person's appendage, and an attachment portion for joining the strap portion to the printable face ply portion to thereby attach said wristband to said person's appendage, the attachment portion including two slots located on opposite sides of a length of the face ply portion and through at least one of which the strap is inserted to affix the wristband to a patient's appendage, at least one of said slots being at least partially surrounded by adhesive.

2. The business form of claim 1 wherein said strap portion and the attachment portion are formed in the lamination layer portion, and the face ply portion includes a layer of face stock adhered to said lamination layer portion.

3. The business form of claim 2 wherein the slots are substantially aligned so that as the lamination portion is folded over the face stock the slots are aligned with the face stock.

4. The business form of claim 3 wherein both of the slots are substantially surrounded by adhesive.

5. The business form of claim 4 further comprising adhesive applied to an outboard end of the strap for adhering the strap end to the wristband after it is inserted through either one or both of said slots.

6. The business form of claim 5 wherein the lamination layer portion includes an overlay portion sized substantially the same as the face stock, and wherein said slots include slots formed in the overlay portion which match and line up with the opposing slots as the overlay portion is folded over the face stock.

7. The business form of claim 6 further comprising a periphery of adhesive on said overlay portion so that as said overlay portion is folded over said face stock said periphery substantially surrounds the face stock.

8. The business form of claim 7 wherein the self-laminating wristband is formed in a carrier sheet, said carrier sheet being comprised of a layer of face stock and a layer of laminating material.

9. The business form of claim 8 wherein said carrier sheet is approximately envelope sized.

10. The business form of claim 8 wherein said carrier sheet is approximately page sized, and further comprising a plurality of self adhering labels applied thereto.

11. A business form containing a self-laminating wristband, said wristband having a laminating layer and an imaging receiving face stock layer, and a cinch for securing the wristband about a person's appendage, said cinch comprising a strap formed in one side of said laminating layer and a pair of slots formed in the opposing side of the laminating layer, one of said slots being substantially surrounded by adhesive so that upon separation from the business form the wristband is assembled by folding over the laminating layer to laminate the face stock layer, inserting the strap through a first slot folding it over onto the strap to adhere it in place, and inserting the strap through the second slot to avoid obscuring the face stock layer wherein the face stock layer includes a tab extending to an inner edge of the first slot so that as said strap is inserted therethrough it is protected from contact with the adhesive substantially surrounding the first slot.

* * * * *

UNITED STATES PATENT AND TRADEMARK OFFICE
CERTIFICATE OF CORRECTION

PATENT NO.         : 7,017,294 B2                                    Page 1 of 1
APPLICATION NO. : 10/627135
DATED              : March 28, 2006
INVENTOR(S)        : James M. Riley It is certified that error appears in the above-identified patent and that said Letters Patent is hereby corrected as shown below:

On page 1, in field (75), replace "James R. Riley" with - - James M. Riley - -.

Signed and Sealed this

Eighth Day of August, 2006

JON W. DUDAS
*Director of the United States Patent and Trademark Office*